(12) United States Patent
Klumperman et al.

(10) Patent No.: US 12,404,354 B2
(45) Date of Patent: Sep. 2, 2025

(54) TERPOLYMERS FOR LIPID NANODISC FORMATION

(71) Applicant: Stellenbosch University, Stellenbosch (ZA)

(72) Inventors: Lubertus Klumperman, Leiderdorp (NL); Gestél Christine Kuyler, Stellenbosch (ZA)

(73) Assignee: Stellenbosch University, Stellenbosch (ZA)

( * ) Notice: Subject to any disclaimer, the term of this patent is extended or adjusted under 35 U.S.C. 154(b) by 0 days.

(21) Appl. No.: 18/719,742

(22) PCT Filed: Dec. 14, 2022

(86) PCT No.: PCT/ZA2022/050068
§ 371 (c)(1),
(2) Date: Jun. 13, 2024

(87) PCT Pub. No.: WO2023/115076
PCT Pub. Date: Jun. 22, 2023

(65) Prior Publication Data
US 2024/0425621 A1    Dec. 26, 2024

(30) Foreign Application Priority Data

Dec. 15, 2021   (GB) .................................. 2118192

(51) Int. Cl.
| | | |
|---|---|---|
| C08F 8/36 | (2006.01) | |
| C07K 1/14 | (2006.01) | |
| C08F 8/32 | (2006.01) | |
| C08F 8/44 | (2006.01) | |

(52) U.S. Cl.
CPC ................ *C08F 8/36* (2013.01); *C07K 1/145* (2013.01); *C08F 8/32* (2013.01); *C08F 8/44* (2013.01); *C08F 2810/50* (2013.01)

(58) Field of Classification Search
None
See application file for complete search history.

(56) References Cited

U.S. PATENT DOCUMENTS

| | | |
|---|---|---|
| 5,049,328 A | 9/1991 | Meyer et al. |
| 2012/0142861 A1 | 6/2012 | Dafforn et al. |
| 2018/0072926 A1 | 3/2018 | Allen et al. |
| 2018/0237653 A1 | 8/2018 | Cloete et al. |
| 2019/0062469 A1 | 2/2019 | Altenberg et al. |

FOREIGN PATENT DOCUMENTS

| | | |
|---|---|---|
| CN | 101759974 A | 6/2010 |
| CN | 103910947 A | 7/2014 |
| CN | 110330759 A | 10/2019 |
| GB | 2562455 A | 11/2018 |
| JP | 2000515181 A  * | 11/2000 |
| JP | 2014139266 A | 7/2014 |
| WO | 2021081329 A1 | 4/2021 |

OTHER PUBLICATIONS

International Search Report and Written Opinion issued in International Application No. PCT/ZA2022/050068, dated Mar. 20, 2023, 9 pages.
Overduin et al., "Advancing membrane biology with poly(styrene-co-maleic acid)-based native nanodiscs", European Polymer Journal vol. 110, pp. 63-68 (2018).
UK Combined Search and Examination Report issued in UK Application No. GB2118192.0, dated Feb. 16, 2022, 7 pages.
Zamfir et al. "Ultra-precise insertion of functional monomers in chain-growth polymerizations", Nature Communications, vol. 3, pp. 1-8 (2012).

* cited by examiner

Primary Examiner — Tae H Yoon
(74) Attorney, Agent, or Firm — McNeill PLLC

(57) ABSTRACT

Terpolymers comprising optionally at least partially substituted styrene repeat units, N-alkylmaleimide repeat units and repeat units selected from the group consisting of maleic anhydride repeat units, maleic acid repeat units or maleic anhydride derivative repeat units and having a narrow molecular weight distribution are provided. The terpolymers may be used to solubilize lipid bilayers to form lipid nanodiscs and isolate membrane proteins.

20 Claims, 14 Drawing Sheets

TERPOLYMERS FOR LIPID NANODISC FORMATION

CROSS-REFERENCE(S) TO RELATED APPLICATIONS

This application is a national phase entry pursuant to 35 USC § 371 of International Application No. PCT/ZA2022/050068, filed Dec. 14, 2022, which claims priority from United Kingdom patent application number 2118192.0 filed on 15 Dec. 2021, each of which is incorporated by reference herein.

FIELD OF THE INVENTION

This invention relates to terpolymers useful for lipid nanodisc formation and investigation. In particular, it relates to terpolymers for solubilising phospholipid bilayers in order to isolate and purify membrane proteins.

BACKGROUND TO THE INVENTION

The isolation of membrane proteins (MPs) from cell membranes has traditionally been carried out by the interaction of the membranes with detergents. This method has significant shortcomings when it comes to the functionality and stability of the MPs. More recently, it was discovered that poly(styrene-co-maleic acid) (SMA) is able to isolate MPs with a layer of native phospholipids, leading to improved functionality and stability of the MPs as described in US2012142861A1.

SMA can be used for solubilising synthetic and biological membranes. SMA solubilises native lipid:protein complexes directly from cells or raw membranes by forming SMALPs. SMALPs are nanoscale disc-shaped lipid assemblies formed from the interaction of membrane lipid bilayers and SMA copolymer. Such polymer-stabilized nanodiscs, commonly termed (SMA) lipid particles (SMALPs) use the amphipathic SMA copolymer to wrap around the lipid tails to stabilize the lipids within a nanodisc structure. The SMA copolymer has statistically arranged styrene and maleic acid groups which are thought to self-assemble into nanodisc structures by intercalating the planar styrene rings into the lipid tails (perpendicular to the plane of the bilayer) with the maleic acid groups allowing solubilization through hydrogen bonding and ionic interactions with the aqueous solvent.

Although the use of SMA has led to significant improvement in the isolation of MPs, there are still shortcomings, such as limited stability in the presence of divalent cations ($Ca^{2+}$, $Mg^{2+}$ etc), limited stability at low and high pH and low-resolution separation in gel electrophoresis (SDS-PAGE), also known as "smearing".

Commercial SMA polymers are produced using a continuous stirred tank reactor (CSTR) which follows conventional free radical polymerization. The conventional free radical polymerization technique results in polymeric material with a large chain length distribution, in terms of which both shorter and longer chains are present within the product sample contributing to an overall large molar mass dispersity. The broad molar mass distribution (MMD) adversely affects the analysis of proteins via gel electrophoresis. When analysing soluble proteins, distinct bands representative of specific proteins are usually observed on the gel. However, integral membrane proteins are more challenging to analyse. Amphiphilic polymers may be used to isolate integral membrane proteins from a cell membrane. Despite conventional SMA and diisobutylene maleic acid (DIMBA) polymers being able to isolate membrane proteins from a cell membrane, these polymers produce smeared bands on the gel, obscuring the exact position of the protein. Additional purification and/or extraction steps of the polymer are needed before analysis to prevent excessive smearing. This contributes to increased analysis time and complexity. Accordingly, there is a need for polymers capable of extracting membrane proteins that alleviate some of the above-mentioned problems, at least to an extent.

The preceding discussion of the background to the invention is intended only to facilitate an understanding of the present invention. It should be appreciated that the discussion is not an acknowledgment or admission that any of the material referred to was part of the common general knowledge in the art as at the priority date of the application.

SUMMARY OF THE INVENTION

In accordance with an aspect of the invention there is provided a terpolymer comprising optionally at least partially substituted styrene repeat units, N-alkylmaleimide repeat units and repeat units selected from the group consisting of maleic anhydride repeat units, maleic acid repeat units or maleic anhydride derivative repeat units, wherein the optionally at least partially substituted styrene repeat units are present in a mol fraction between and including 0.50 and 0.55 and wherein the terpolymer has a narrow molecular weight distribution characterised by a dispersity (Đ) of less than or equal to 1.4 as determined by size exclusion chromatography (SEC) using N,N-dimethylformamide as mobile phase.

The alkyl group in the N-alkylmaleimide repeat units may be a benzyl group or a linear or branched $C_4$-$C_{10}$ alkyl group. The N-alkylmaleimide repeat units are preferably N-benzylmaleimide repeat units.

The maleic anhydride derivative repeat units may be N-alkyl maleimide derivatives with a different alkyl group to that of the N-alkylmaleimide repeat units. The N-alkyl maleimide derivatives may be further substituted. The maleic anhydride derivative repeat units may be N—(N',N'-disubstituted amino-alkyl)-maleimide) derivatives. Alternatively, the maleic anhydride derivative repeat units are alkyl maleates. Further alternatively, the maleic anhydride derivative repeat units may include a zwitterionic moiety. The zwitterionic moiety may be a carboxybetaine, sulfobetaine or phosphobetaine. The carboxybetaine may be an ammoniocarboxylate.

The mole fraction of N-alkylmaleimide repeat units in the terpolymer may be between 0.05 and 0.40.

The terpolymer may have the general structure of formula (I):

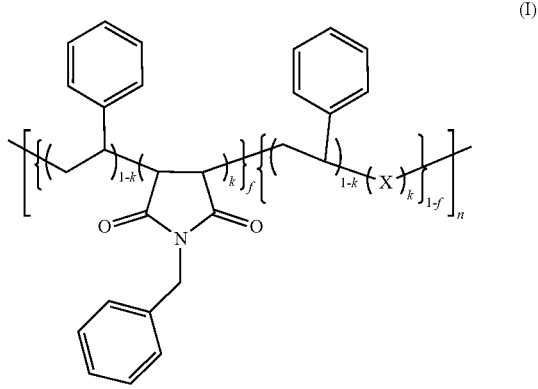

in which the mol fraction of N-benzylmaleimide (f) is between 0.05 and 0.40, the mol fraction of maleic anhydride in the base polymer (k) is between and including 0.45 and 0.50, and X is selected from the group consisting of

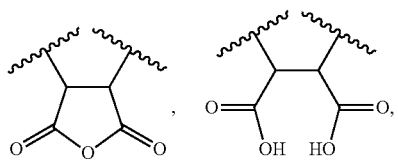

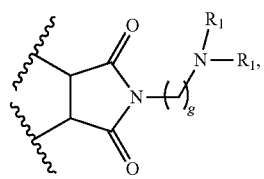

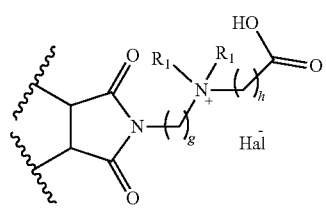

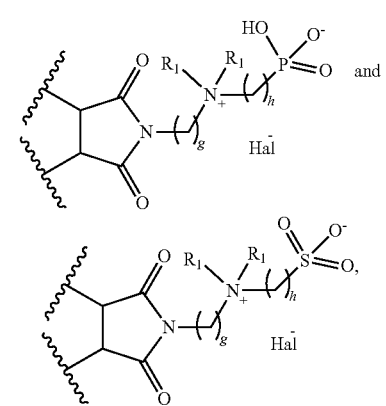

in which g is an integer between and including 2 and 7;

h is an integer between and including 1 and 6;

$R_1$ is a branched or linear $C_1$-$C_4$ alkyl; and

Hal⁻ is a halide anion selected from the group consisting of bromide (Br⁻), chloride (Cl⁻) and iodide (I⁻).

It is preferred that g is 2 or 3; h is 2 or 3; or $R_1$ is a methyl or ethyl group. In particular, X may be represented by one of the following structures

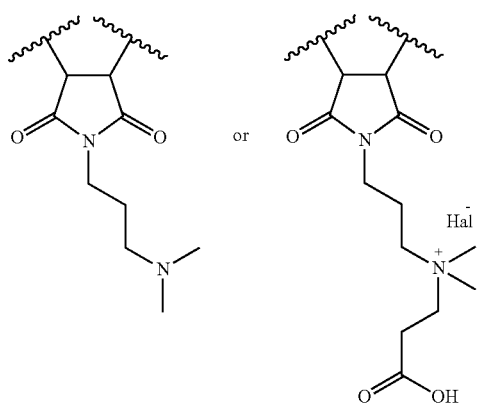

in which Hal⁻ is a halide anion selected from (Br⁻), chloride (Cl⁻) and iodide (I⁻).

The number average molecular weight of the terpolymer may be equal to or less than 10 kDa.

The number average molecular weight of the terpolymer may range between and including 1 kDa and 10 kDa.

In accordance with a second aspect of the invention, there is provided a method of synthesizing a terpolymer as described above, the method comprising the steps of:

reacting a precursor copolymer of optionally at least partially substituted styrene repeat units present in a mol fraction between and including 0.50 and 0.55 and maleic anhydride repeat units, the precursor copolymer having a narrow molecular weight distribution characterized by a dispersity (Đ) of less than or equal to 1.4, with a selected molar amount of alkyl amine to form a terpolymer which includes a selected mole fraction of N-alkylmaleimide repeat units; and optionally hydrolysing or further modifying remaining maleic anhydride repeat units in the terpolymer.

The molar amount of alkyl amine added is selected to produce a partially derivatized terpolymer in which the mole fraction of N-alkylmaleimide repeat units ranges between and including 0.05 and 0.40. The alkyl amine may be benzyl amine or a linear or branched $C_4$-$C_{10}$ alkyl amine, preferably benzyl amine.

The precursor copolymer may be a substantially alternating styrene maleic anhydride (SMAnh) polymer. The precursor copolymer may have a maleic anhydride mole fraction between and including 0.45 and 0.50. The precursor copolymer may be a RAFT-polymerized styrene maleic anhydride (SMAnh) copolymer. The RAFT moiety end group of the RAFT-polymerized styrene maleic anhydride (SMAnh) copolymer may be removed prior to the reaction with alkylamine to form the terpolymer.

The method may further include the step of hydrolysing or further modifying the remaining maleic anhydride repeat units in the terpolymer. The remaining maleic anhydride repeat units may be hydrolysed to maleic acid repeat units in the presence of a base.

Alternatively, the method may include the step of modifying the remaining maleic anhydride repeat units into N-alkyl maleimide derivative repeat units with a different alkyl group to that of the N-alkylmaleimide repeat units. The remaining maleic anhydride repeat units may also be modified into N—(N',N'-disubstituted amino-alkyl)-maleimide) derivative repeat units. More particularly, the remaining maleic anhydride repeat units may be imidized to N—(N', N'-dimethyl-3-aminopropyl)-maleimide repeat units by reacting the terpolymer with 3-(N,—N-dimethylamino)propyl-1-amine (DMAPA).

Further alternatively, the remaining maleic anhydride repeat units may be modified to include a zwitterionic moiety. The zwitterionic moiety may be a carboxybetaine, sulfobetaine or phosphobetaine. The zwitterionic carboxybetaine moiety may be an ammoniocarboxylate formed by first reacting the terpolymer with N,N-disubstituted aminoalkyl-1-amine to obtain a modified terpolymer in which the maleic anhydride repeat units have been imidized to N—(N', N'-disubstituted amino-alkyl)-maleimide) repeat units and then reacting the modified terpolymer with a ω-halo-alkanoic acid to produce a terpolymer including zwitterionic ammoniocarboxylate moieties. More particularly, the method may include the steps of first reacting the remaining maleic anhydride repeat units with DMAPA to form the imidized terpolymer with N—(N',N'-dimethyl-3-aminopropyl)-maleimide repeat units and then reacting the imidized terpolymer with 3-bromopropanoic acid to produce a terpolymer including zwitterionic dimethylammoniopropylate groups.

In accordance with a third aspect of the invention there is provided a method of isolating a membrane protein from a lipid bilayer, the method comprising mixing the lipid membrane including a membrane protein with an aqueous solution of the above-described terpolymer or a terpolymer prepared according to the above-described method.

In accordance with a fourth aspect of the invention there is provided a method of solubilising a lipid bilayer optionally including one or more membrane proteins, the method comprising mixing the lipid bilayer with an aqueous solution of the above-described terpolymer or with a terpolymer prepared according to the above-described method to produce nanodiscs.

The lipid bilayer may be a cell membrane, optionally including membrane proteins, and the nanodiscs produced may be native nanodiscs.

Embodiments of the invention will now be described, by way of example only, with reference to the accompanying drawings.

DETAILED DESCRIPTION WITH REFERENCE TO THE DRAWINGS

Figure 1:
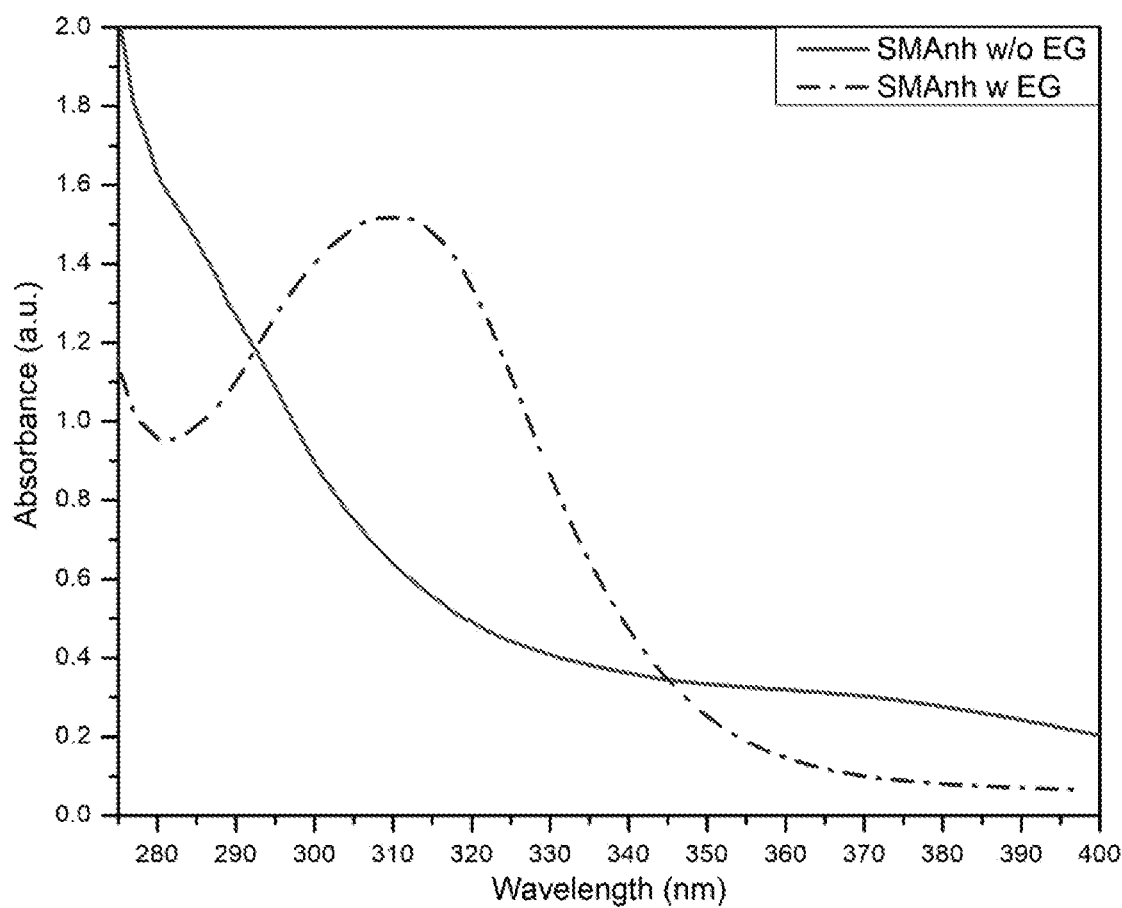
FIG. 1 is a UV absorbance spectrum before and after RAFT end-group removal from the RAFT-synthesized styrene maleic anhydride (SMAnh) polymer.

Terpolymers are provided in which the polymer backbone comprises three different repeat units, namely (i) optionally at least partially substituted styrene repeat units, (ii) N-alkylmaleimide repeat units and (iii) repeat units selected from the group consisting of maleic anhydride repeat units, maleic acid repeat units or maleic anhydride derivative repeat units. As used herein, the term "terpolymer" should be interpreted to mean a polymer comprising three different repeat units in any type of sequence. The optionally at least partially substituted styrene repeat units may be present in a mol fraction between and including 0.50 and 0.55 in the terpolymers. The terpolymers have a narrow molecular weight distribution characterised by a dispersity (Ð) of less than 2, preferably characterised by a dispersity (Ð) of less than or equal to 1.4, as determined by size exclusion chromatography using N,N-dimethylformamide as mobile phase, as described in Scheuing, D. R., Size exclusion chromatography of polyelectrolytes in dimethylformamide. *J. Appl. Polym. Sci.*, 1984, 29, 2819-2828 (https://doi.org/10.1002/app.1984.070290912). The narrow molecular weight distribution may be obtained by controlling the chain length of the precursor styrene maleic anhydride (SMAnh) polymer that is modified to produce the terpolymers. For example, the terpolymers may be derived from a precursor substantially alternating SMAnh polymer synthesized by RAFT-polymerisation to better control chain length and obtain a narrow molecular weight distribution.

Accordingly, a base terpolymer is provided which can be modified in a variety of different ways as may be required for the use of the terpolymer to solubilise lipid membranes and isolate membrane proteins. The base polymer is preferably a substantially alternating copolymer of styrene repeat units and maleic anhydride repeat units with a styrene mol fraction of between and including 0.50 and 0.55 and a maleic anhydride mol fraction between and including 0.45 and 0.50 partially modified into N-alkylmaleimide derivative repeat units, wherein the substantially alternating copolymer of styrene and maleic anhydride has a narrow molecular weight distribution characterized by a dispersity (Ð)<2, and preferably a dispersity (Ð) s 1.4. The remaining maleic anhydride repeat units which were not modified into N-alkylmaleimide derivative repeat units may subsequently be modified in many different ways, which includes: (i) hydrolysis into maleic acid repeat units; (ii) conversion into a tertiary amine functional N-alkyl maleimide; or (iii) conversion into a zwitterionic derivative, such as a zwitterionic functional N-alkyl maleimide.

The extent of derivatization of the original maleic anhydride repeat units into either N-alkylmaleimide repeat units, maleic acid repeat units or maleic anhydride derivative repeat units can be determined by standard techniques for chemical analysis, such as elemental analysis, Fourier-transform infrared spectroscopy and $^1$H nuclear magnetic resonance spectroscopy or a combination of such techniques.

The alkyl group of the N-alkylmaleimide repeat units forming part of the terpolymer may be a benzyl group or a linear of branched $C_4$-$C_{10}$ alkyl group. The branched alkyl group may for example be isopropyl, isobutyl, tert-butyl or neopentyl or the like. The alkyl of N-alkylmaleimide repeat units is preferably benzyl, so that the repeat units are N-benzylmaleimide repeat units.

The styrene repeat units may be at least partially substituted and may, for example be α-methylstyrene, p-methylstyrene, p-methoxystyrene, p-chlorostyrene, p-bromostyrene, p-tert-butylstyrene or the like. In a preferred embodiment, the terpolymers include unsubstituted styrene repeat units.

In some embodiments, the maleic anhydride derivative repeat units of the terpolymer are alkyl maleates. In other embodiments, the maleic anhydride derivative repeat units are N-alkyl maleimide derivatives. The alkyl of the N-alkyl maleimide derivatives should of course be different to the alkyl of the N-alkylmaleimide repeat units so that the polymer is a terpolymer having three different repeat units in its backbone. The maleic anhydride derivative repeat units are preferably tertiary amine functional N-alkyl maleimides such as N—(N',N'-disubstituted amino-alkyl)-maleimide) derivatives. More particularly, the maleic anhydride derivative repeat units may be N—(N',N'-di($C_1$-$C_4$)alkyl-amino-($C_2$-$C_7$)alkyl)-maleimide repeat units, such as N—(N',N'-dimethyl-3-aminopropyl)-maleimide repeat units.

In some embodiments, the maleic anhydride derivative repeat units include a zwitterionic moiety. The zwitterionic moiety may be an a carboxybetaine such as ammoniocarboxylate, a sulfobetaine such as ammoniosulphonate or a phosphobetaine such as ammoniophosphonate. Ammoniocarboxylates are overall neutral groups that can be incorporated in a polymer and have a permanently positively charged ammonium cation and a negatively charged carboxylate group which is not adjacent to the cationic site. The pendant zwitterionic ammoniocarboxylate moieties may have the following general structure:

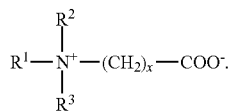

The equivalent sulphonate and phosphonate derivatives are similar, possessing the following respective structures:

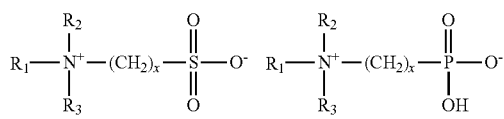

The terpolymer may have the general structure of formula (I):

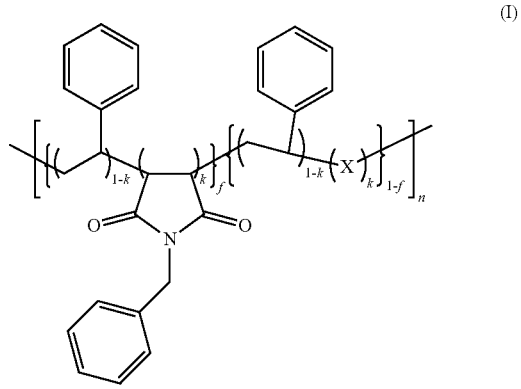

in which f is between and including 0.05 and 0.40, k is between and including 0.45 and 0.50 and X is selected from the group consisting of

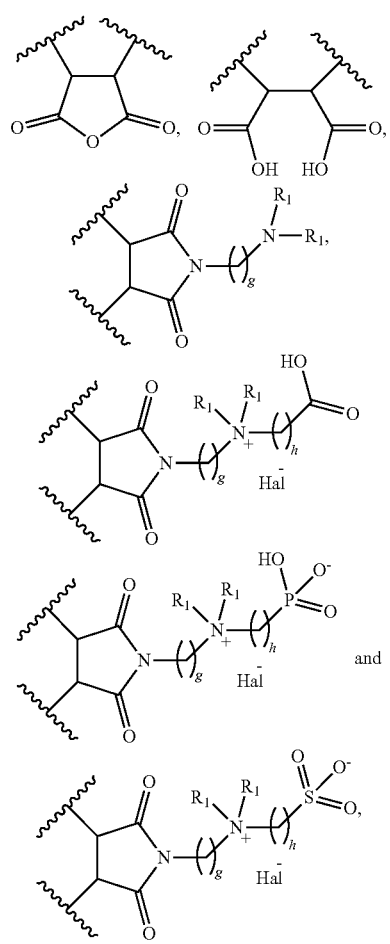

in which g is an integer between and including 2 and 7;
h is an integer between and including 1 and 6;
$R_1$ is a branched or linear $C_1$-$C_4$ alkyl; and
Hal$^-$ is a halide anion selected from the group consisting of bromide (Br$^-$), chloride (Cl$^-$) and iodide (I$^-$).

In the formula (I), f is the mole fraction of N-benzylmaleimide derivative repeat units in the copolymer and n is the number average degree of polymerization. The mole fraction of N-benzylmaleimide (f) is preferably between 0.25 and 0.40. The mole fraction of styrene in formula (I) is 0.5 and the mole fraction of N-benzylmaleimide derivative repeat units and the maleic acid derivative repeat units combined is 0.5. Therefore, the mole fraction of maleic acid derivative repeat units may range between and including 0.10 and 0.45, but preferably is between and including 0.10 and 0.25.

In particular, X may be

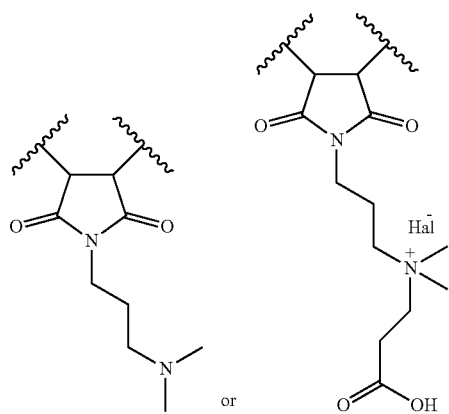

in which Hal$^-$ is a halide anion selected from the group consisting of bromide (Br$^-$), chloride (Cl$^-$) and iodide (I$^-$).

The number average molecular weight of the terpolymer may range between and including 1 kDa and 10 kDa. More particularly, the number average molecular weight of the terpolymer may range between and including 1.5 kDa and 6 kDa. Accordingly, the number-average degree of polymerization (n) may range between and including 7 and 25.

A method of synthesizing terpolymers is provided which comprises reacting a precursor copolymer of optionally at least partially substituted styrene repeat units and maleic anhydride repeat units with a selected molar amount of alkyl amine to form a terpolymer which includes (i) optionally at least partially substituted styrene repeat units; and (ii) a selected mole fraction of N-alkylmaleimide derivative repeat units. The optionally at least partially substituted styrene repeat units are preferably present in a mol fraction between and including 0.50 and 0.55. The precursor copolymer preferably has a narrow molecular weight distribution characterized by a dispersity (Đ) of less than 2, and more preferably less than or equal to 1.4 as determined by SEC. The molar amount of alkyl amine added is selected to produce a partially derivatized polymer, i.e., a terpolymer, in which the mole fraction of N-alkylmaleimide repeat units ranges between and including 0.05 and 0.40, preferably between and including 0.25 and 0.40.

A preferred alkyl amine is benzyl amine. A reaction of the precursor copolymer with a selected molar amount of benzyl amine may be carried out in a suitable solvent and dropwise addition of a benzyl amine solution at a select temperature between and including 10° C. and 50° C., preferably between and including 20 and 45° C., for a selected time between and including 0.5 and 4 hours, preferably between and including 1-3 hours. Subsequently, the reaction mixture is stirred at an elevated temperature for a selected time. This subsequent heating and stirring step results in ring closure and may be carried out at a temperature within the range of, and including, 100° C. to 160° C., preferably between and including 120 and 155° C., for 1 to 6 hours, preferably for 2 to 5 hours. A remaining mole fraction of maleic anhydride repeat units is initially formed. The precursor copolymer may be a substantially alternating styrene maleic anhydride (SMAnh) copolymer with a maleic anhydride mol fraction between and including 0.45 and 0.50, i.e., poly(styrene-alt-maleic anhydride), with a narrow molecular weight distribution (MWD) characterized by a dispersity of less than 2, preferably less than or equal to 1.4 (Đ≤1.4). The precursor SMAnh copolymer may be synthesized by RAFT polymerization to obtain the desired molecular weight distribution. The RAFT moiety end group of the RAFT-polymerized styrene maleic anhydride (SMAnh) polymer may be removed prior to the reaction with benzylamine to form the terpolymer. The RAFT end-group may be cleaved off through one of several well-known techniques, including thermolysis and radical-induced reduction and the resultant SMAnh used as a precursor or parent copolymer for producing the terpolymers. The SMAnh copolymer has a substantially alternating sequence (predominantly MSM triads) as confirmed by microstructure analysis of the resonance of the aromatic carbon closest to the polymer backbone and the methylene carbon between the styrene and maleic anhydride repeat units on the aliphatic backbone where the resonances appeared at δ=137.0-140.0 ppm and δ=33.0-37.0 ppm, respectively, on the $^{13}$C NMR spectrum of the SMAnh copolymer.

Since only a selected mole fraction of the maleic anhydride repeat units are derivatized to N-alkylmaleimide repeat units, and preferably N-benzylmaleimide repeat units, a remaining mole fraction of maleic anhydride repeat units is initially formed. To form the other terpolymers, the method may include the further step of hydrolysing or further modifying the remaining maleic anhydride repeat units in the terpolymer. The remaining mole fraction of maleic anhydride repeat units may be hydrolysed to maleic acid repeat units in the presence of a base such as a sodium hydroxide solution. Alternatively, the remaining mole fraction of maleic anhydride repeat units may be modified into N-alkyl maleimide derivative repeat units or N—(N',N'-disubstituted amino-alkyl)-maleimide) derivative repeat units by reacting it with ω—(N,N-dialkyl amino)alkyl-1-amine as described herein below with reference to the first step in producing the zwitterionic maleic anhydride derivative repeat units. In particular, the remaining mole fraction of maleic anhydride repeat units may be imidized to N—(N', N'-dimethyl-3-aminopropyl)-maleimide repeat units by reacting the terpolymer with 3-(N,—N-dimethylamino)propyl-1-amine (DMAPA).

Further alternatively, the remaining mole fraction of maleic anhydride repeat units may be modified to include a zwitterionic moiety. The zwitterionic moiety may be an ammoniocarboxylate formed by reacting the terpolymer with N,N-disubstituted aminoalkyl-1-amine to form a modified terpolymer in which the maleic anhydride repeat unit units have been imidized to N—(N'N'-disubstituted amino-alkyl)-maleimide) repeat units and reacting the modified terpolymer with a ω-halo-alkanoic acid to produce a terpolymer including zwitterionic ammoniocarboxylate moieties. Similar zwitterionic moieties can be introduced by utilizing the equivalent phosphonic acid or sulphonic acid instead of the halo-alkanoic acid.

The modification of the remaining mole fraction of maleic anhydride into its zwitterionic derivative therefor occurs in two steps. The first step may be a reaction with ω—(N,N- dialkyl amino)alkyl-1-amine. This reaction can take place over a period of 3-5 hours in water or in polar organic solvents such as dimethylformamide (DMF), dimethylsulfoxide, butanone, acetone or dioxane at a temperature within the range of and including 110-170° C. In solvents with a boiling point below the reaction temperature, the reaction needs to be conducted under sufficient pressure to prevent the reaction mixture from boiling. Preferably, the reaction is conducted for 1 to 6 hours in DMF at 120-150° C. and at atmospheric pressure or up to 0.5 MPa or in water at 120-170° C. and 0.4 to 1 MPa pressure, and most preferably in DMF at 130-140° C. and at atmospheric pressure or up to 0.4 MPa. The second step is the reaction with an ω-halo-alkanoic acid, such as 3-bromopropanoic acid. This reaction may be conducted in a polar solvent at a temperature of between 25 to 75° C. for a period of and including 15 to 35 hours. Preferred solvents for this second step are DMF and water.

More particularly, the remaining mole fraction of maleic anhydride repeat units may be modified by reacting the remaining maleic anhydride repeat units with N,N-di($C_1$-$C_4$)alkyl-amino($C_2$-$C_7$)alkyl-1-amine to form styrene maleimide intermediate (SMI) repeat units, more specifically N—(N',N'-di($C_1$-$C_4$)alkyl-amino-($C_2$-$C_7$)alkyl)-maleimide repeat units, and then the SMI intermediate repeat units are reacted with a ω-halo-alkanoic acid, preferably a ω-bromo-, ω-chloro-, or ω-iodo-($C_2$-$C_7$)alkanoic acid, to produce zwitterionic derivative repeat units of the terpolymer. More specifically, the method may include the steps of reacting the remaining mole fraction of maleic anhydride repeat units with DMAPA to form the imidized terpolymer with N—(N', N'-dimethyl-3-aminopropyl)-maleimide repeat units and then reacting the imidized terpolymer with 3-bromopropanoic acid to produce a terpolymer including zwitterionic dimethylammoniopropylate groups. Accordingly, the remaining mole fraction of maleic anhydride repeat units are imidized to N—(N',N'-dimethyl-3-aminopropyl)-maleimide by treatment with 3-(N,—N-dimethylamino)propyl-1-amine (DMAPA) to afford a styrene maleimide (SMI) intermediate and the resulting tertiary amine functionality on the SMI intermediate quaternized with 3-bromopropanoic acid to yield the zwitterionic carboxybetaine moiety.

The terpolymers described herein or prepared according to the methods described herein may be used in a method to solubilise lipid systems and form nanodiscs by mixing a lipid bilayer optionally containing membrane proteins with an aqueous solution of a selected terpolymer to produce nanodiscs. The nanodiscs are synthetic structures composed of a section of lipid bilayer, often containing a membrane protein, which is surrounded by an outer rim of a stabilising polymer, i.e. one of the terpolymers described herein. The lipid nanodiscs formed with the terpolymers comprise a lipid bilayer encircled or encased or otherwise formed into a nanodisc by a terpolymer. The lipid bilayer may be a cell membrane, optionally including membrane proteins, and the nanodiscs produced may be native nanodiscs.

To most effectively solubilise a lipid bilayer into relatively stable lipid nanodiscs in an aqueous medium, the ratio between the optionally at least partially substituted styrene repeat units (preferably styrene repeat units), N-benzylmaleimide repeat units and the and the maleic anhydride, maleic acid or maleic anhydride derivative repeat units in the terpolymer may be within the range of and including 10:1:9 to 5:4:1 (i.e. 0.05<f<0.4), preferably and including 2:1:1 to 5:4:1 (i.e. 0.25<f<0.4) and the terpolymer may have a number average molecular weight that is equal to or less than 10 kDa.

In particular, the terpolymer encircling the lipid bilayer section in the lipid nanodisc may have the general formula (I):

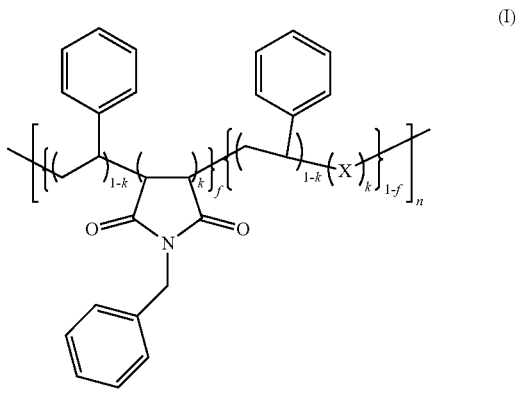

in which X is selected from the group consisting of

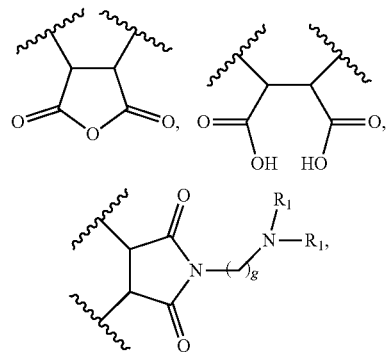

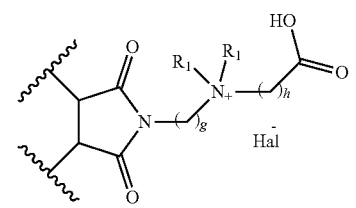

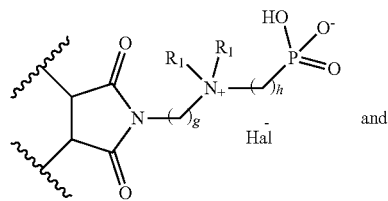

and

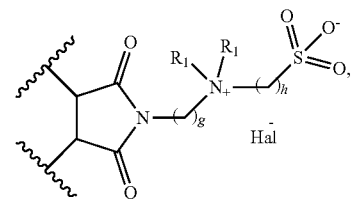

in which g is an integer between and including 2 and 7;

h is an integer between and including 1 and 6;

$R_1$ is a branched or linear $C_1$-$C_4$ alkyl;

$Hal^-$ is a halide anion selected from the group consisting of bromide ($Br^-$), chloride ($Cl^-$) and iodide ($I^-$);

f is the mole fraction of N-benzylmaleimide derivative repeat units in the copolymer and is preferably between and including 0.05 and 0.40;

k is the mol fraction of maleic anhydride repeat units in the base copolymer (poly(styrene-alt-maleic anhydride)) and is between and including 0.45 and 0.50; and n is the number average degree of polymerization.

In particular, X may be

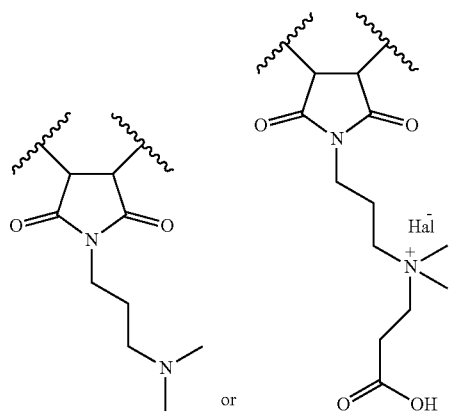

or in which $Hal^-$ is a halide anion selected from the group consisting of bromide ($Br^-$), chloride ($Cl^-$) and iodide ($I^-$).

Depending on the structure of the terpolymer, the resultant lipid nanodiscs may be stable in a particular pH range and in an aqueous medium or solution containing multivalent cations. In particular, the resultant lipid nanodiscs may be stable in the presence of divalent metal cations such as $Mg^{2+}$ and $Ca^{2+}$ at specific concentrations. The pH and ionic stability of the nanodiscs may depend on the structure of the terpolymer, in particular the choice of third repeat unit (besides the optionally substituted styrene and N-benzylmaleimide repeat units). The molar ratio of the three different repeat units and the number average molecular weight of the terpolymer may also be varied, amongst other factors, to finetune nanodisc stability.

For example, a terpolymer of formula (I) with X being a maleic acid repeat unit forms lipid nanodiscs that are stable at 5≤pH≤10 and $[Mg^{2+}]$≤20 mM. A terpolymer of formula (I) with X being a N—(N',N'-dimethyl-3-aminopropyl)-maleimide repeat unit forms lipid nanodiscs that are stable at 5≤pH≤8 and $[Mg^{2+}]$≥100 mM. A terpolymer of formula (I) with X being a zwitterionic functional N-alkyl maleimide such as:

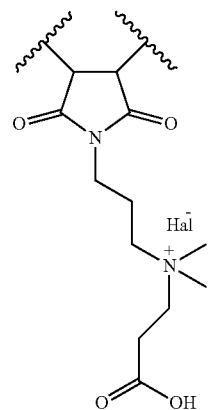

forms lipid nanodiscs that are stable at a wider pH range of 3≤pH≤10 and $[Mg^{2+}]$≥100 mM.

The terpolymers described herein may be used in a method of isolating a membrane protein from a lipid bilayer, particularly from cell membranes. The method comprises mixing the cell membrane including a membrane protein with an aqueous solution of the terpolymer. The terpolymers described herein provide a high-resolution separation on SDS-PAGE (little smearing) due to the narrow molecular weight distribution of the terpolymers characterized by a dispersity (Đ) s 1.4.

EXAMPLES

For reasons of clarity, structures in the Examples are shown as alternating copolymers, although also here, substantially or close to alternating copolymers are a more accurate description of the products.

Materials and Characterization

Maleic anhydride (MAnh) briquettes (99%, Sigma-Aldrich) and 2,2'-azobis(2-butyronitrile) (AIBN) were purified via recrystallization from toluene and methanol, respectively, and were dried under vacuum overnight. Styrene (St) (99%, Sigma Aldrich) monomer inhibitor was removed by passing through a basic aluminium oxide column prior to use. Benzyl amine (99%, Sigma Aldrich), 2-butanone (≥99%, Sigma-Aldrich), 1,3,5-trioxane (≥99%, Sigma Aldrich), N,N-dimethylformamide (DMF) (99.8%, anhydrous, Sigma Aldrich), and deuterated acetone-$d_6$ (99.9%, MagniSolv™ were used as received. The RAFT agent S-butyl-S'-(1-phenyl ethyl) trithiocarbonate (BPT) was synthesized as described in literature (Postma, A. et al. Synthesis of Well-Defined Polystyrene with Primary Amine End Groups through the Use of Phthalimido-Functional RAFT Agents. *Macromolecules* 39, 5293-5306 (2006)).

Poly(styrene-co-maleic anhydride) (SMAnh) with a 2:1 styrene to maleic anhydride ratio (Cray Valley, UK) was hydrolysed before use and used as a control. XIRAN™ 30010 in a 20% solution (referred to as SMA 3:1) (Polyscope, EU) was used as a control. All other chemicals and reagents were purchased from Sigma-Aldrich, unless stated otherwise.

Samples were characterized by attenuated total reflectance fourier transform infrared (ATR-FTIR) spectroscopy using a Thermo Nicolet iS10 Smart iTR spectrometer with diamond/ZnSe internal reflection crystal ATR accessory. Spectra were recorded from 600-4000 cm$^{-1}$ with a spectral resolution of 4 cm$^{-1}$, utilizing 64 individual scans. Omnic™ computer software (V 8.1) was used for data acquisition and processing.

Liquid state nuclear magnetic resonance (NMR) analysis was performed on a Varian™ VXR-Unity (300 MHz) at 25° C. to obtain $^1$H NMR and quantitative $^{13}$C NMR spectra. Deuterated acetone ((CD$_3$)$_2$CO) was used for the analysis of all polymers. Approximately 50 mg of each sample was dissolved in 0.7 mL of deuterated solvent.

Synthesis Methods (i) Poly(Styrene-alt-Maleic Anhydride) (SMAnh)
Typical RAFT Polymerization Procedure:

In a 250 mL 3-necked round-bottom flask fitted with an ice water condenser, and oil bubbler; a solution of MAnh (9.81 g, 100 mmol), St (10.4 g, 100 mmol), BPT (1.08 g, 4.00 mmol), AIBN (0.131 g, 0.800 mmol), and 1,3,5-trioxane (0.320 g, 3.52 mmol) in 72 mL 2-butanone was prepared. Copolymerizations were performed at a solids content of 30% w/v with a RAFT:initiator ratio of 5:1 and 1.5% w/w 1,3,5-trioxane as an internal reference standard. The solution was degassed by purging with argon gas (45 min) while stirring. The reaction was allowed to react for 24 hours at 80° C. while stirring. The reaction was terminated by cooling and exposure to atmospheric oxygen. The copolymer was isolated from the reaction mixture by precipitation in cold isopropanol (3×750 mL), followed by vacuum filtration. The resultant copolymer was dried in vacuo at 40° C. overnight to yield a fine pale-yellow powder. Subsequently, the RAFT moiety at the ω-chain end (Z-group) was removed, yielding an off-white powder.

(ii) General Synthesis of Poly(Styrene-Co-Maleic Acid-Co-(N-Benzyl)Maleimide) (BzAm-SMAnh):

2 grams of RAFT-polymerized SMAnh (end-group (EG) removed) was dissolved in 8 mL DMF in a 3-necked 50 mL round-bottom flask fitted with an oil bubbler under magnetic stirring. Varying molar amounts of benzyl amine (Table 1) was mixed with a small amount of DMF before being added dropwise to the solution. Gas evolution and a colour change from light to darker orange could be observed upon the addition of the amine. The reaction mixture was allowed to stir at 30° C. for 1 hour, producing the ring-opened version of the terpolymer. The reaction mixture was subsequently heated to 130° C. and allowed to stir for an additional 3 hours. Another colour change from dark to lighter yellow/orange was observed upon heating. This resulted in the ring-closed maleimide moieties. The terpolymers were isolated from the reaction mixture by precipitation in cold diethyl ether (3×100 mL), followed by either vacuum filtration or centrifugation. The resultant terpolymers were dried in vacuo at 40° C. overnight to yield an array of yellow powders.

Scheme 1: RAFT synthesis of SMAnh and subsequent end-group removal.

Scheme 2: Amine modification and subsequent ring closure.

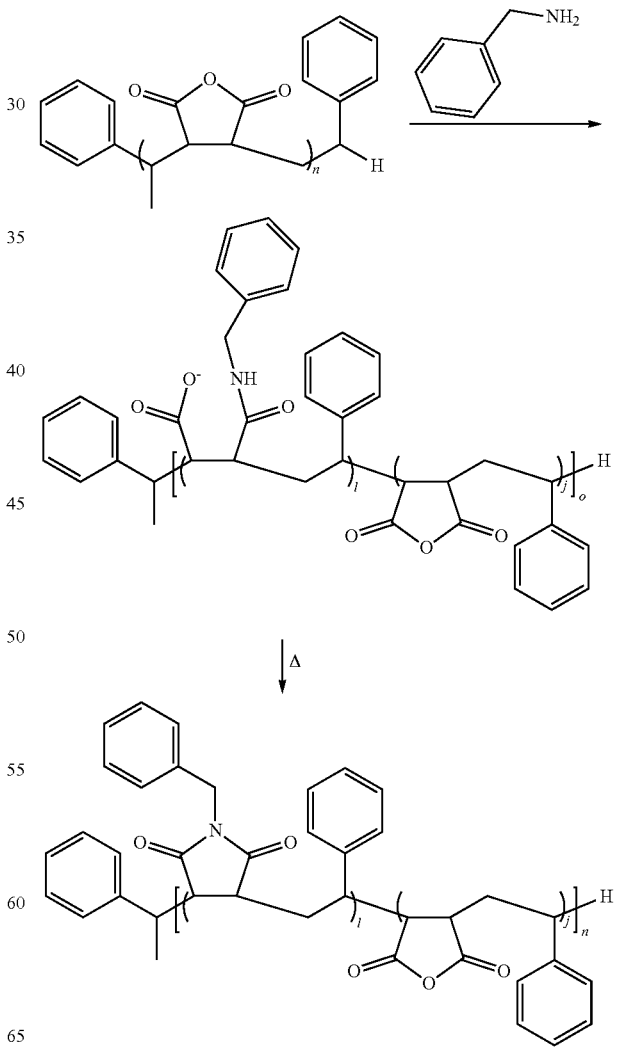

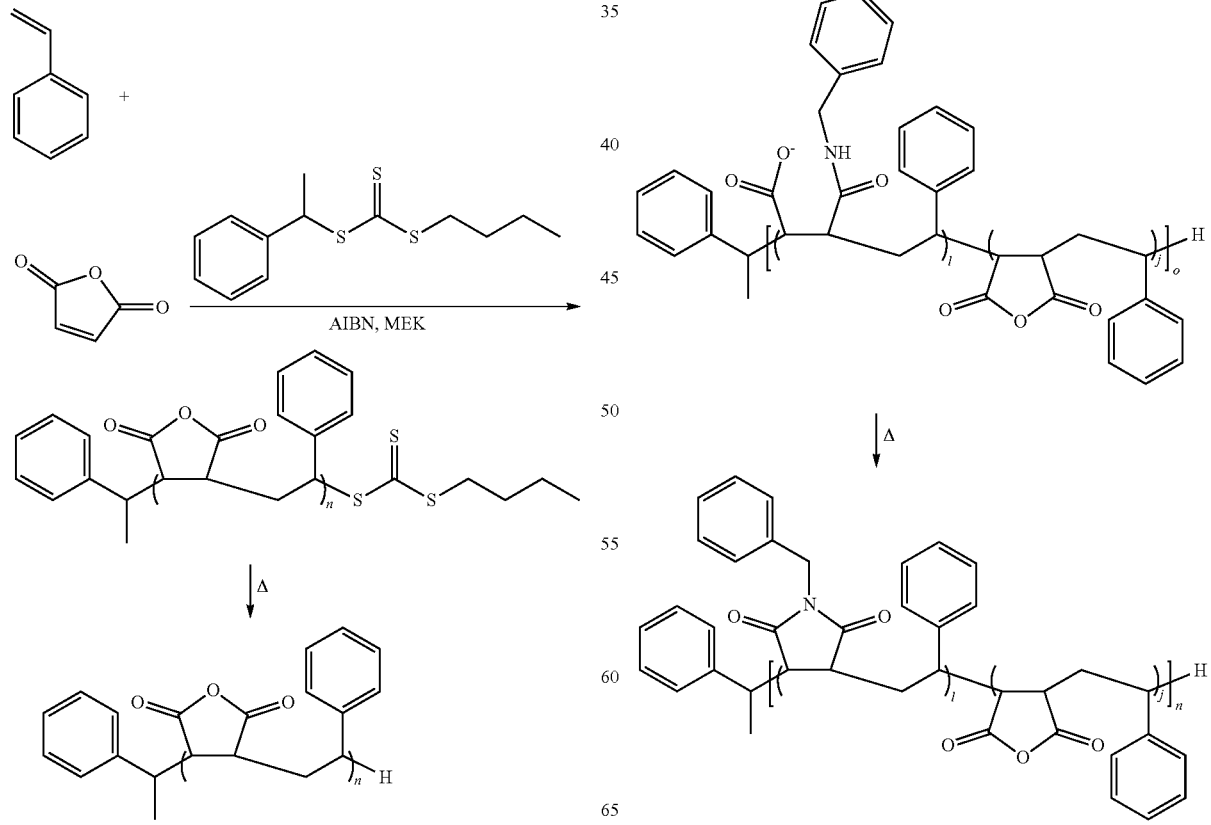

TABLE 1

Monomer molar ratios used in the functionalization of SMAnh to produce a series of terpolymers with varying hydrophobicity.

| Sample | Monomer molar ratios (mol fractions) | | | f |
|---|---|---|---|---|
| | Styrene | Benzyl amine | Maleic anhydride | |
| 0.25 BzAm | 0.5 | 0.125 | 0.375 | 0.250 |
| 0.30 BzAm | 0.5 | 0.150 | 0.350 | 0.300 |
| 0.35 BzAm | 0.5 | 0.175 | 0.325 | 0.350 |
| 0.40 BzAm | 0.5 | 0.200 | 0.300 | 0.400 |

(iii) Synthesis of Amphiphilic BzAm-SMAnh Derivatives (1a) Carboxylic Acid Derivative (R=Benzyl)

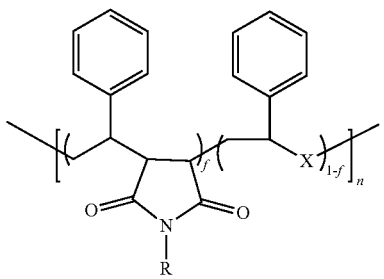

(1)

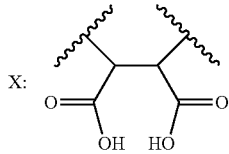

(a)

Hydrolysis of BzAm-SMAnh was carried out via standard procedures. Briefly, 20 mL aqueous 0.1 mM NaOH solution was added to 0.30 BzAm (1 g, 3.1 mmol MAnh equivalents) in a round-bottom flask and refluxed for 6 hours. Thereafter the mixture was allowed to cool to room temperature.

The polymer was isolated via lyophilisation.

(1b) Tertiary Amine Derivative (R=Benzyl)

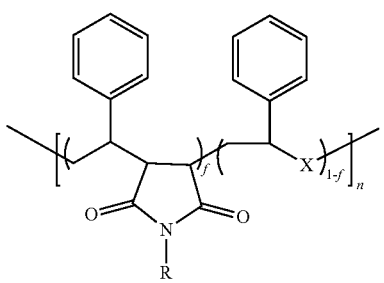

(1)

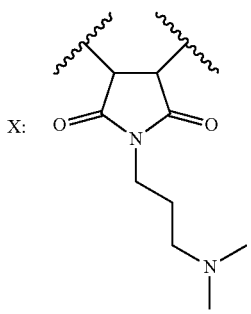

(b)

Modification of BzAm-SMAnh into a tertiary amine derivative is conducted via a procedure similar to the BzAm modification. Briefly, 0.30 BzAm (1 g, 3.1 mmol MAnh equivalents) is added to a round-bottom flask, containing 10 mL anhydrous DMF. After dissolution of the polymer, DMAPA (0.32 g, 3.1 mmol) is added dropwise and the mixture gradually heated to 130° C. The mixture is stirred for 3 h and cooled down to room temperature. The polymer is isolated via precipitation in cold diethyl ether (100 mL).

(1c) i) Zwitterionic Derivative (R=Benzyl)

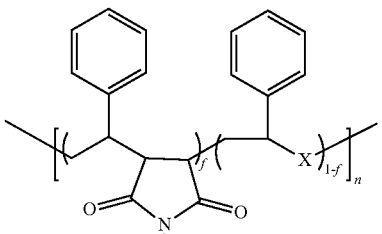

(1)

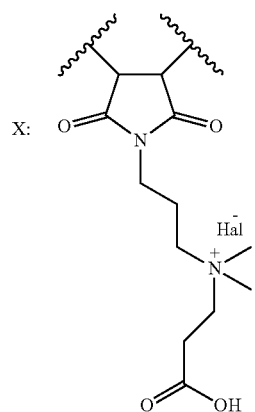

(c)

The zwitterionic derivative is synthesized by modification of the tertiary amine derivative (1b). Briefly, in a round-bottom flask, compound 1b (0.50 g, 1.2 mmol equivalent tertiary amine) is dissolved in 10 mL DMF. In a separate beaker, 3-bromopropionic acid (0.18 g, 1.2 mmol) is dissolved in 5 mL DMF and transferred to a dropping funnel. The 3-bromopropionic acid solution is slowly added to the polymer solution over a period of 30 minutes. The reaction mixture is stirred for 20 h at 50° C. After 20 h, the solution is cooled to room temperature. The polymer is isolated via precipitation in cold diethyl ether (100 mL).

(1c) ii) Sulfobetaine Zwitterionic Derivative (R=Benzyl)

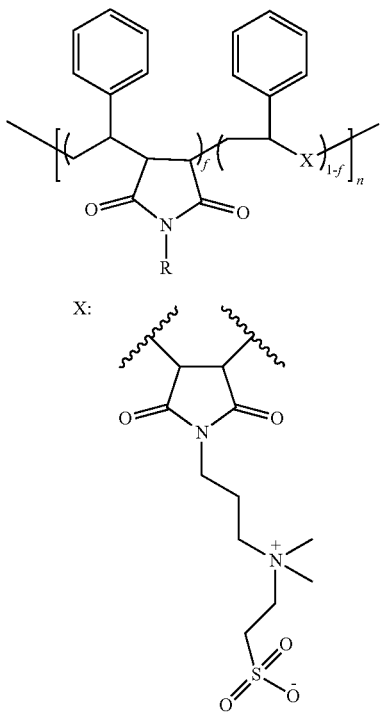

The sulfobetaine zwitterionic derivative is synthesized by modification of the tertiary amine derivative (1b). Briefly, in a round-bottom flask, compound 1b (0.50 g, 1.2 mmol equivalent tertiary amine) is dissolved in 10 mL dry chloroform. In a separate beaker, 1,3-propanesultone (0.15 g, 1.2 mmol) is dissolved in 5 mL chloroform and transferred to a dropping funnel. The 1,3-propanesultone solution is slowly added to the polymer solution over 30 minutes. The reaction mixture is stirred for 20 h at room temperature, during which a white precipitate forms. After 20 h, the polymer is isolated via vacuum filtration and subsequent chloroform washing (2×100 mL). The resultant terpolymers are then dried in vacuo at room temperature overnight.

Results

The first step in producing a well-defined polymer series is the production of a well-defined base polymer, in this case, SMAnh. Table 2 summarizes the details of the base polymer before and after the removal of the RAFT end-group (EG). Visual comparison of the base polymer with and without the RAFT end-group suggest the removal of the end-group as the thiocarbonylthio containing SMAnh has a distinct pale yellow colour. This assumption is supported by the respective molecular weight and UV data. Molecular weight data obtained by size exclusion chromatography (SEC) correlate well with the target values. The slight decrease in molecular weight for the SMAnh without EG is to be expected as the terminal thiocarbonylthio containing group was successfully cleaved to yield the sulphur-free chain end functionality. The molecular weight data and insignificant change in dispersity values indicate that no evident bimolecular termination occurred as this would result in high molecular weight peaks in the SEC traces. The UV absorbance spectra in FIG. 1 confirm successful cleavage through the disappearance of the characteristic thiocarbonyl absorbance maxima at 310 nm.

TABLE 2

Molecular weight, dispersity, and appearance of SMAnh with and without the RAFT end-group.

| Sample | $M_{n, target}$ (g/mol) | Conversion[a] (%) | $M_{n, SEC}$[b] (g/mol) | $M_{w, SEC}$[b] (g/mol) | Đ[b] | Appearance |
|---|---|---|---|---|---|---|
| SMAnh w EG | 5 326 | 93 | 5 000 | 6 800 | 1.36 | Pale yellow |
| SMAnh w/o EG | | | 4300 | 5 800 | 1.35 | Off-white |

[a]Conversion was determined by $^1$H-NMR.
[b]Molecular weight and dispersity values were obtained by size exclusion chromatography (SEC) with DMF as mobile phase and poly(methyl methacrylate) (PMMA) calibration standards.

Thorough characterization and confirmation of successful EG removal of the base polymer allow for the production of the desired terpolymer series by subsequent amine modifications.

Figure 2:
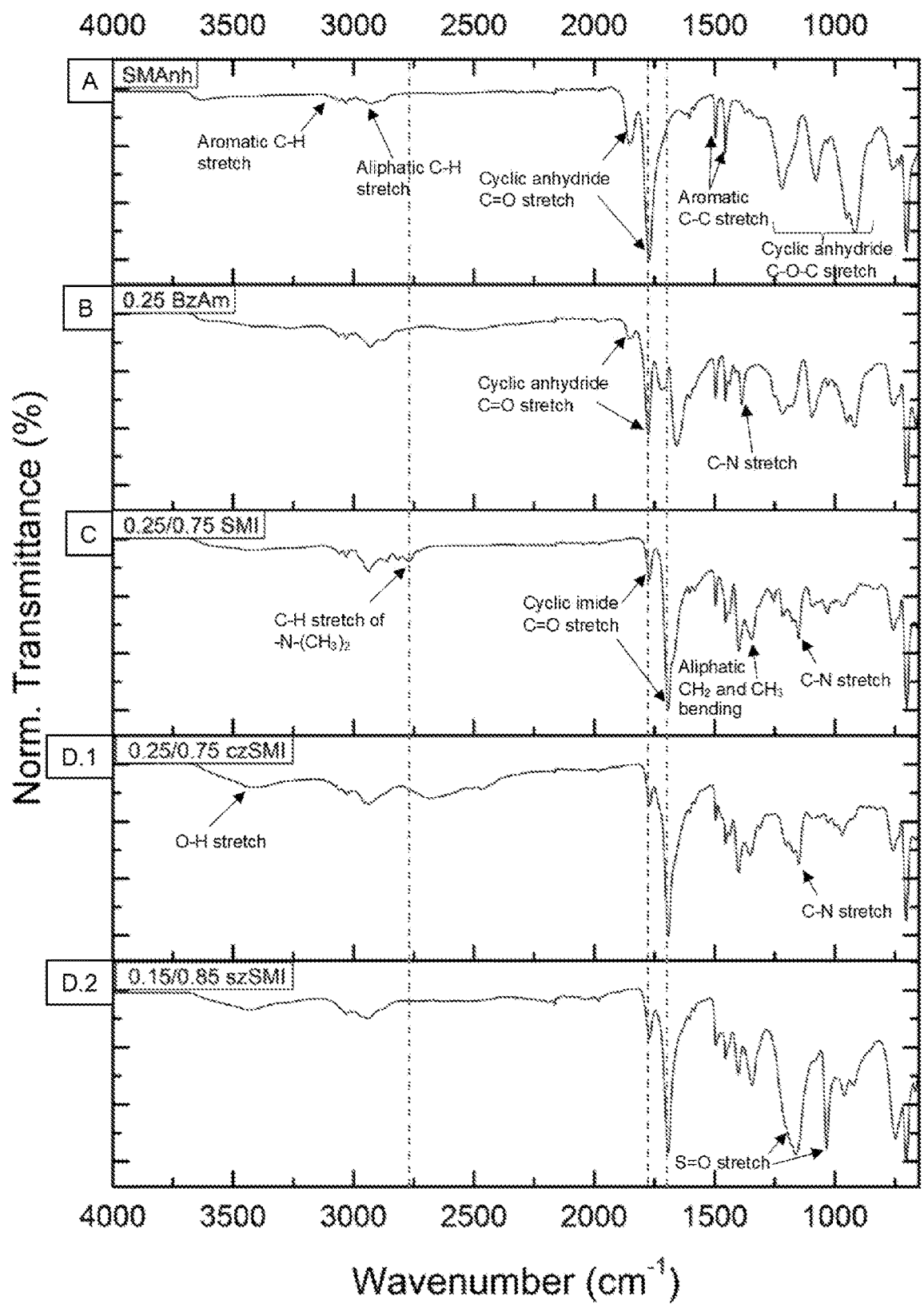
FIG. 2 is ATR-FTIR spectra of the (A) SMAnh base polymer, (B) 0.25 BzAm terpolymer, (C) 0.25/0.75 SMI terpolymer, (D.1) 0.25/0.75 carboxybetaine zwitterionic terpolymer, and (D.2) 0.15/0.85 sulfobetaine zwitterionic terpolymer.

FIG. 2 shows the normalized ATR-FTIR spectra of (A) the alternating SMAnh base polymer without the RAFT end-group, (B) 0.25 BzAm, (C) 0.25/0.75 SMI, (D.1) 0.25/0.75 czSMI, and (D.2) 0.15/0.85 szSMI.

The partial modification of the anhydride moieties of SMAnh is characterized by the reduced peak intensities of the carbonyl peaks at 1852 and 1771 cm$^{-1}$ and the reduced peak intensity of the cyclic anhydride C—O—C stretching bands between 1315 and 840 cm$^{-1}$. Subsequent maleimide formation is shown by the partial shift of the C=O carbonyl anhydride peak to 1771 and 1716 cm$^{-1}$. The increased peak intensity of the aromatic C—C stretching bands between 1494 and 1453 cm$^{-1}$ is expected with an overall increase in aromatic moieties with an increasing degree of benzyl amine modification. As only ~25% of the available MAnh moieties are modified, it is expected that both the C=O and imide stretching bands, as well as the C—O—C stretching bands are still present in spectrum (B). In spectrum (C) the residual MAnh moieties are converted to maleimides through the reaction with DMAPA to form the SMI derivative. The complete conversion of all available MAnh moieties is confirmed by the complete disappearance of the anhydride C=O peaks at 1852 and 1771 cm$^{-1}$ and the appearance of two strong peaks at 1769 and 1693 cm$^{-1}$ that correspond to the cyclic maleimide formation. The appearance of an additional peak at 2760 cm$^{-1}$ correlates to the C—H stretch of the —N(CH$_3$)$_2$ of the tertiary amine.

Spectrum (D.1) in FIG. 2 shows conversion of SMI to the carboxybetaine zwitterionic terpolymer (czSMI) where the appearance of a broad O—H stretch peak centred around 3400 cm$^{-1}$ relates to the presence of the carboxylic acid moiety. The disappearance of the peak at 2760 cm$^{-1}$ supports the conversion of the tertiary amine while maintaining the strong cyclic imide C=O peaks at 1769 and 1693 cm$^{-1}$.

Spectrum (D.2) in FIG. 2 shows the conversion from SMI to the sulfobetaine zwitterionic terpolymer (szSMI). The expected maleimide C=O stretching peaks are visible at 1769 and 1693 cm$^{-1}$. The absorbance peaks at 1167 cm$^{-1}$ and 1034 cm$^{-1}$ correspond to S=O stretching vibrations.

Figure 3:
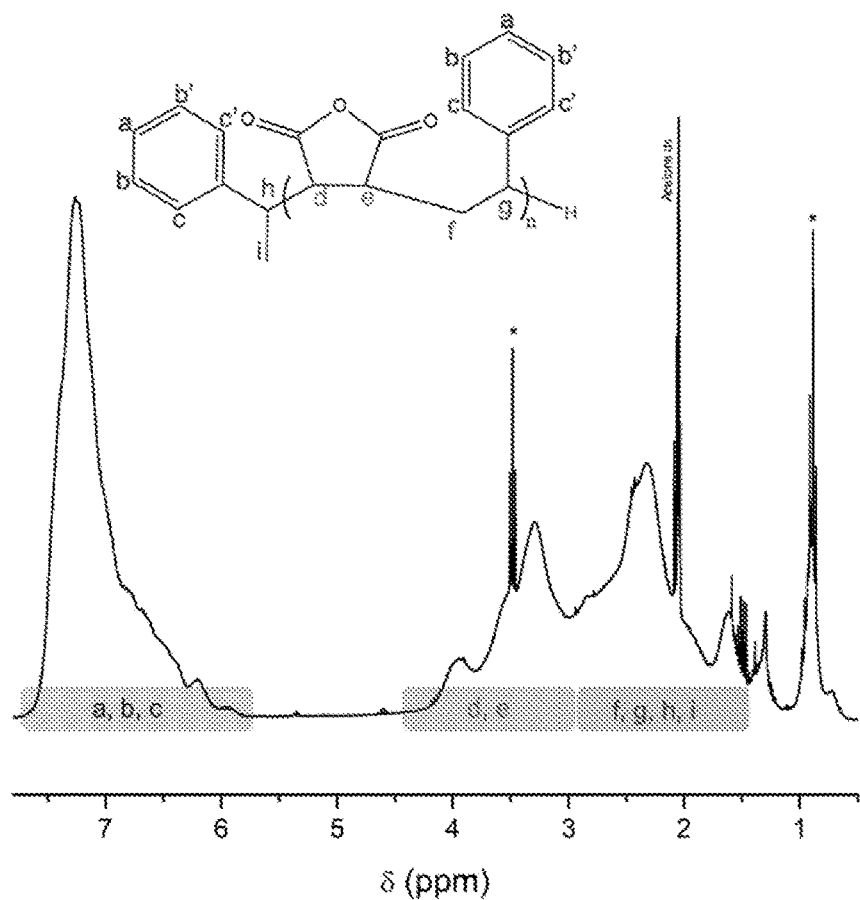
FIG. 3 is an $^1$H-NMR (300 MHz, $(CD_3)_2CO$) spectrum of SMAnh without the RAFT end-group (*trace impurities)
Figure 4:
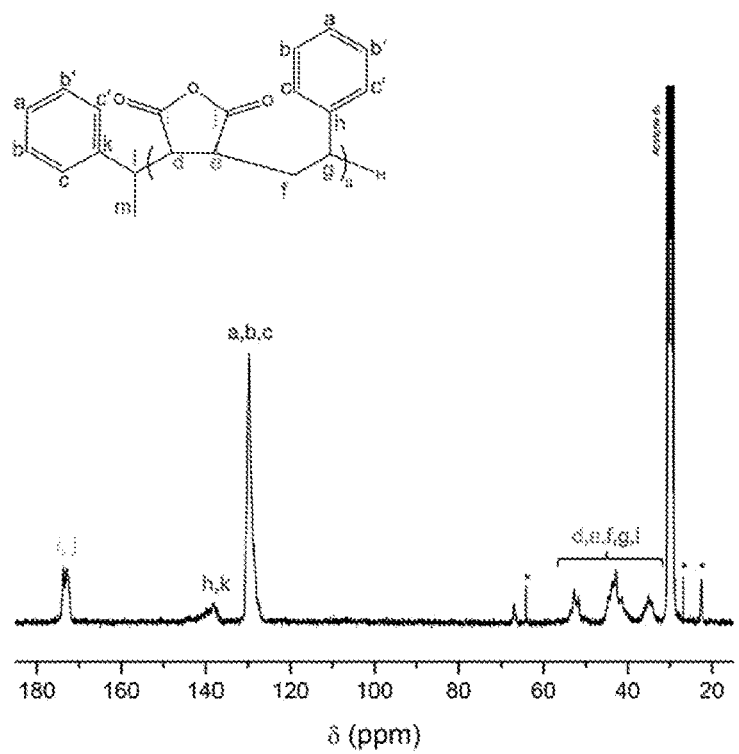
FIG. 4 is an q-$^{13}$C-NMR (300 MHz, $(CD_3)_2CO$) spectrum of SMAnh without the RAFT end-group (*trace impurities)

FIG. 3 and FIG. 4, respectively, show the $^1$H-NMR and quantitative $^{13}$C-NMR spectra of the SMAnh base polymer used for subsequent modification. In FIG. 3 the typical broad SMAnh backbone peaks are seen between 1.45-2.98 ppm corresponding to the styrenic backbone and between 3.00-4.25 ppm relating to that of maleic anhydride. The broad peak between 5.80-7.73 ppm can be attributed to the aromatic protons of the styrene substituents as well as the RAFT R-group.

Figure 5:
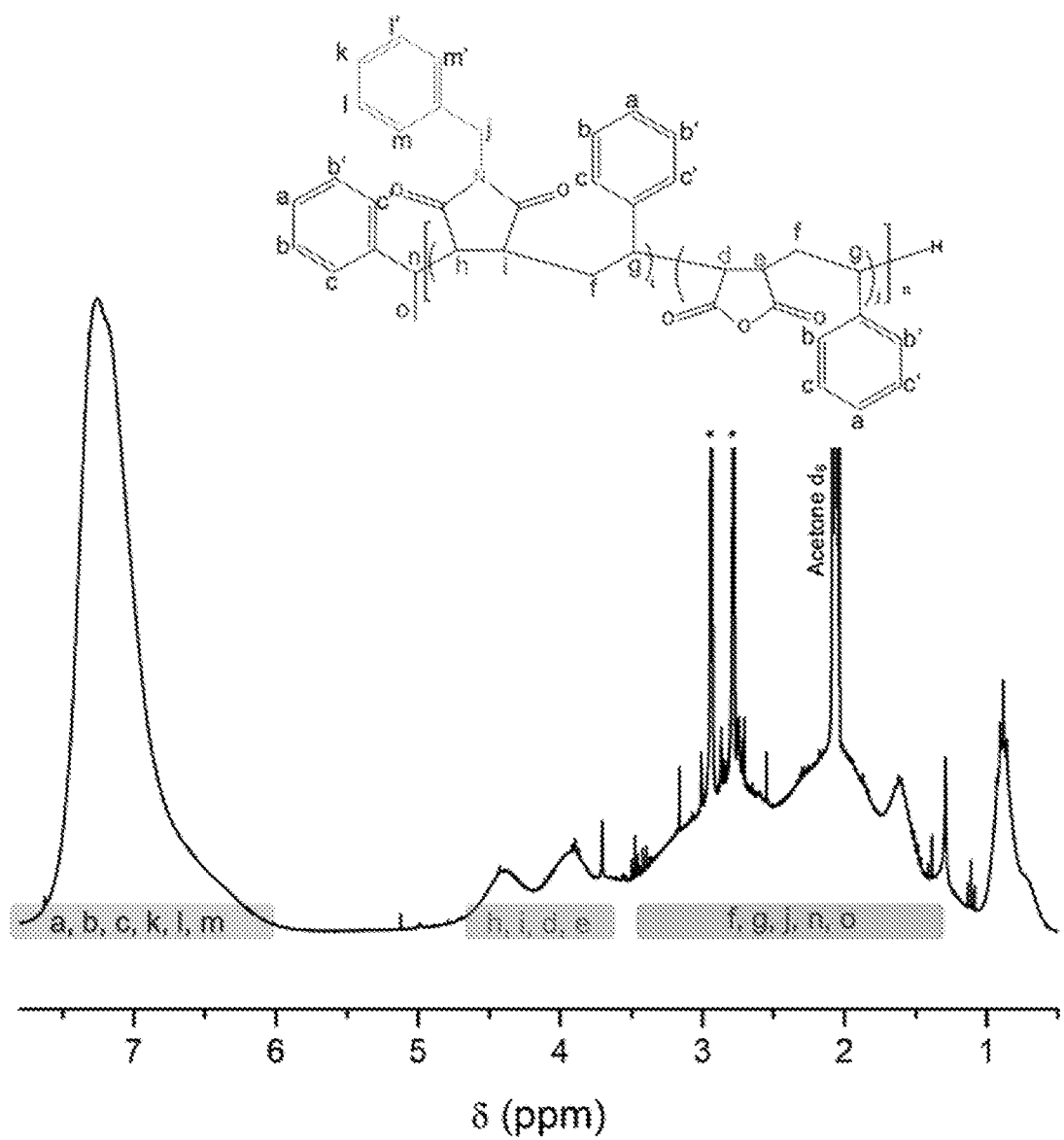
FIG. 5 is an $^1$H-NMR (300 MHz, $(CD_3)_2CO$) spectrum of the 0.25 BzAm sample (*trace impurities)
Figure 6:
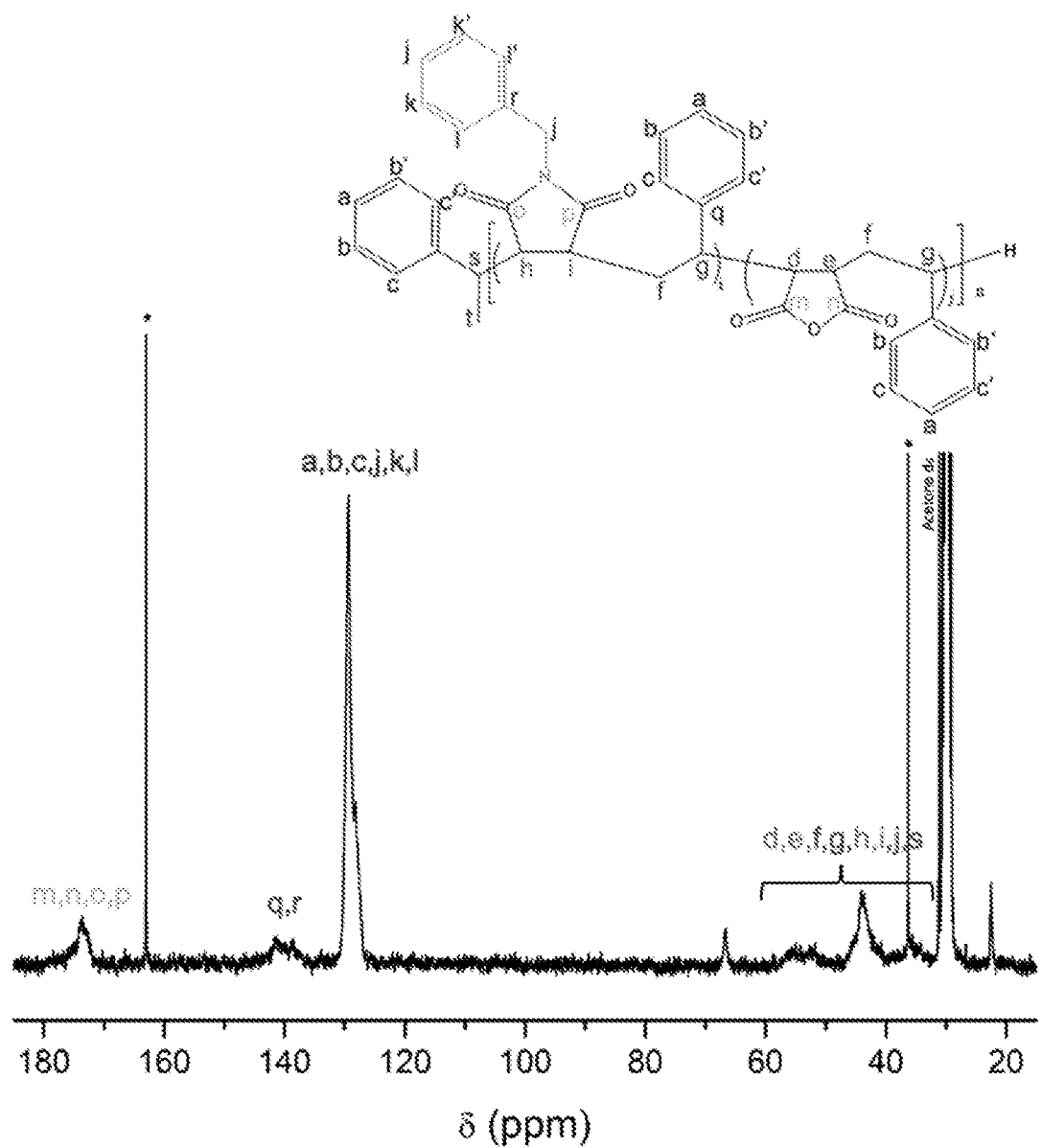
FIG. 6 is an $^{13}$C-NMR (300 MHz, $(CD_3)_2CO$) spectrum of the 0.25 BzAm sample (*trace impurities)

As an example, the $^1$H-NMR and q-$^{13}$C-NMR spectra of one of the terpolymers are shown in FIG. 5 and FIG. 6. FIG. 5 shows the 25% modified version of the base polymer, the 0.25 BzAm sample. There is an apparent shift in the broad peak corresponding to the backbone MAnh protons to between 3.63-4.90 ppm and relates to the partial functionalization of MAnh yielding the maleimide moieties dispersed along the backbone. In addition to this, there is an apparent increase in the peak intensity of the aromatic region around 5.82-7.76 ppm as the number of aromatic substituents increase with increasing benzyl amine content.

FIG. 4 and FIG. 6, respectively, show the quantitative $^{13}$C-NMR spectra of the base polymer and the subsequently functionalized 0.25 BzAm sample. In FIG. 6, the broadening of the backbone protons between 32.84 and 54.47 ppm is indicative of the residual maleic anhydride and additional maleimide moieties. The large peak between 126.47 and 131.05 ppm corresponds to the aromatic carbons of both the styrenic and benzylic protons present in the 0.25 BzAm. In FIG. 4, the characteristic carbonyl anhydride peaks can be seen at 172.38 ppm. In FIG. 6, the slight, but indicative downfield shift and broadening of this peak to 174.00 ppm confirm the partial conversion of anhydride to imide. The peak broadening signifies the presence of residual anhydride carbonyls in addition to the newly formed imides.

Biochemical Analysis
Methods
(i) Polymer Hydrolysis

The residual maleic anhydride moieties of all BzAm polymers underwent hydrolysis to achieve the water-soluble maleic acid moiety before conducting biophysical analyses. The hydrolysis protocol has been reported in literature (Kopf, A. H., Koorengevel, M. C., van Walree, C. A., Dafforn, T. R. & Killian, J. A. A simple and convenient method for the hydrolysis of styrene-maleic anhydride copolymers to styrene-maleic acid copolymers. *Chemistry and Physics of Lipids* 218, 85-90 (2019)). Scheme 3 illustrates the resultant terpolymer structure.

Scheme 1: Hydrolysis of the residual maleic anhydride moieties yielded the water-soluble terpolymer.

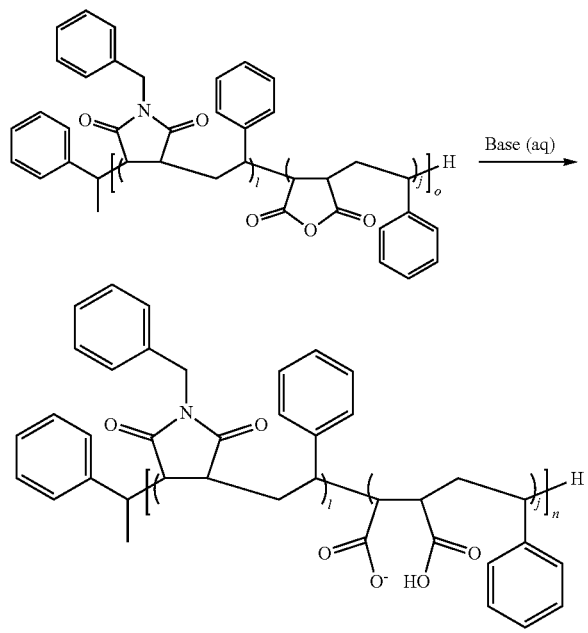

(ii) Membrane Solubilization and Nanodisc Characterization
Dynamic Light Scattering Dynamic light scattering experiments were performed using a DynaPro™ Plate Reader Ill and DYNAMICS software (Wyatt Technology, Haverhill, UK), using the laser wavelength of 825.4 nm with a detector angle of 150°. Each sample (40 µL) was loaded into a 384-well glass bottom SensoPlate™ (Greiner™ Bio-One, Germany) in triplicate. Each measurement consisted of 5 scans of 5 s, carried out at 25° C., with the attenuator position and laser power automatically optimized for size determination (nm).

Liposome Preparation

Lyophilised DMPC (Avanti™ Polar Lipids, USA) were measured using an analytical balance and suspended in chloroform, with 1 mL of chloroform being added per 10 mg of lipid. Chloroform was evaporated from the lipid solution using an air tap. The lipids were resuspended in 50 mM Tris, 150 mM NaCl pH 7.4 buffer (or required buffer for pH stability investigations) using a water sonicator bath to make a 10 mg/mL solution. The lipid solution was separated into 1 mL aliquots and vesicles were formed by conducting 5 freeze-thaw cycles using the −80° C. freezer, followed by a thawing step at 42° C. using a heat block. The vesicle solution was then extruded with 11 passes of the solution through 200 nm nuclepore track-etched polycarbonate membranes if required (Avanti™ Polar Lipids, USA).

pH Stability pH experiments were conducted as described in literature, ranging from pH 4 to 10 (Fiori, M. C., Jiang, Y., Altenberg, G. A. & Liang, H. Polymer-encased nanodiscs with improved buffer compatibility. *Scientific Reports* 7, (2017)). The stability of the polymer-liposome solutions was determined by measuring the optical density of the solution at 620 nm using a UV/vis spectrophotometer (DeNovix™ DS-11+ microvolume spectrophotometer).

Buffer Solutions of Different pH Values were Made Up as Follows:

pH 4 and 5 was achieved using a solution of 50 mM of sodium acetate 50 mM and 150 mM NaCl. pH 6 and 7 was achieved using a solution of 50 mM $KH_2PO_4/K_2HPO_4$ and 150 mM NaCl. pH 8 and 9 was achieved using a solution of 50 mM Tris/HCl 50 mM and 150 mM NaCl. pH 10 was achieved using a solution of 50 mM CHES/NaOH and 150 mM NaCl.

Ionic Stability

Ionic stability experiments were conducted as reported in literature with $MgCl_2$ concentrations ranging from 0-50 mM.[3] Ionic stability of polymer-liposome solutions was determined by measuring the optical density of the solution at 620 nm using a UV/vis spectrophotometer (DeNovix™ DS-11+microvolume spectrophotometer).

Solubilisation of Lipid Vesicles

Polymer solutions (5% w/v) were prepared using the required buffer. These polymer solutions were then added to an equal volume of DMPC at 1.25 mg/mL and incubated in a cold room overnight. Following DMPC solubilisation, the samples were spun at 10,000 g for 30 mins to pellet out any insolubilised material prior to analysis.

Solubilisation and Purification of Membrane Proteins (ZipA)

The production, expression and purification of *E. coli* membranes induced for the overexpression of Hiss-tagged (C-terminus) ZipA, was adapted from literature (Lee, S. C. et al. Nano-encapsulated *Escherichia coli* Divisome Anchor ZipA, and in Complex with FtsZ. *Scientific Reports* 9, 1-16 (2019)). Briefly, membranes containing 40 mg total protein were incubated overnight at 4° C. with an equal volume of 50 mM Tris, 150 mM NaCl, pH 7.5, 2.5% (w/v) polymer whilst rotating. Following solubilisation samples were spun at 10,000×g for 30 mins to pellet out any insolubilised material. The supernatant was incubated for 1 hour at 4° C. with Ni-NTA resin whilst rotating. Using SigmaPrep™ spin columns equilibrated in Buffer A (50 mM Tris, 150 mM NaCl, pH 7.5), the lysate was loaded onto the equilibrated spin column and centrifuged at 270×g for 5 minutes, and flowthrough collected. The resin was washed twice at 890×g for 2 minutes with 600 ul of Buffer A containing 20 mM imidazole. Elution of SMA(LP)-ZipA required 2 wash steps at 890×g for 2 minutes with 300 ul of Buffer A containing 500 mM imidazole. Elution fractions containing SMA(LP) ZipA were analysed by SDS-PAGE to assess purity. Densitometric analysis, if required, was achieved using ImageJ.

Results

To assess the ability of the terpolymers to form nanodiscs, initial solubilization experiments were conducted using 1,2-dimyristoyl-sn-glycero-3-phosphocholine (DMPC) liposomes. Dynamic light scattering (DLS) allowed the determination of the resultant nanodisc sizes and was found to be 8±3 nm. Turbidimetric analyses were used to investigate the effect of pH and varying divalent cation (magnesium cations, $Mg^{2+}$) concentrations on the resultant polymer-bound nanodiscs.

Figure 7:
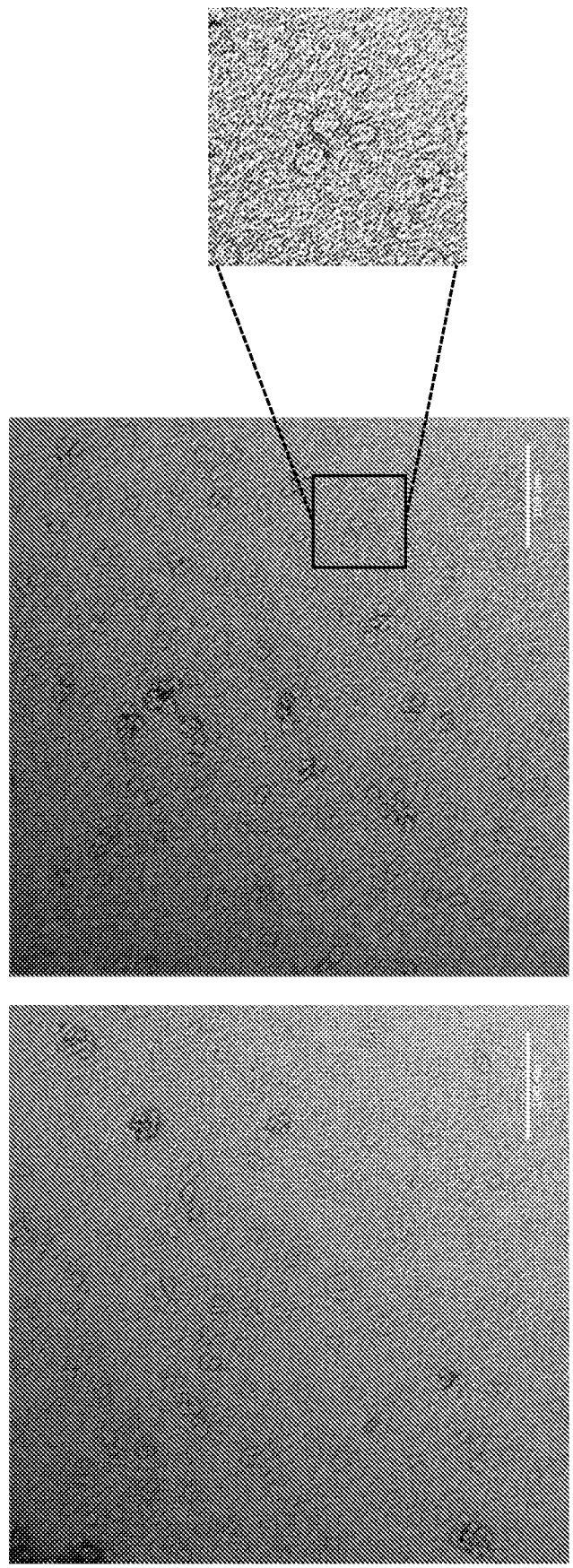
FIG. 7 are TEM images of the nanodiscs formed by the 0.25 BzAm-SMA sample (magnification×80K, scale bars indicate 100 nm)

Increased turbidity signals are indicative of nanodisc destabilization as a result of polymer precipitation and the consequent precipitation of nanodisc lipid components. Nanodiscs could be visualized by using transmission electron microscopy (TEM), while also providing complementary nanodisc size data (FIG. 7). These results are summarised in Table 3. Finally, the membrane solubilisation efficiency of the terpolymer series was assessed by gel electrophoresis.

TABLE 3

Soluble pH and divalent cation range as determined by turbidimetric analyses and DMPC nanodisc sizes determined by DLS.

| Sample | Soluble pH range | $Mg^{2+}$ stability (mM) | Nanodisc size (nm) |
|---|---|---|---|
| SMA2:1 (control) | 5-10 | 0-15 | 8 ± 3 |
| 0.25 BzAm | 5-10 | 0-20 | 8 ± 3 |
| 0.30 BzAm | 5-10 | 0-20 | 8 ± 3 |
| 0.35 BzAm | 5-10 | 0-15 | 8 ± 3 |
| 0.40 BzAm | 5-10 | 0-15 | 8 ± 3 |

Figure 8:
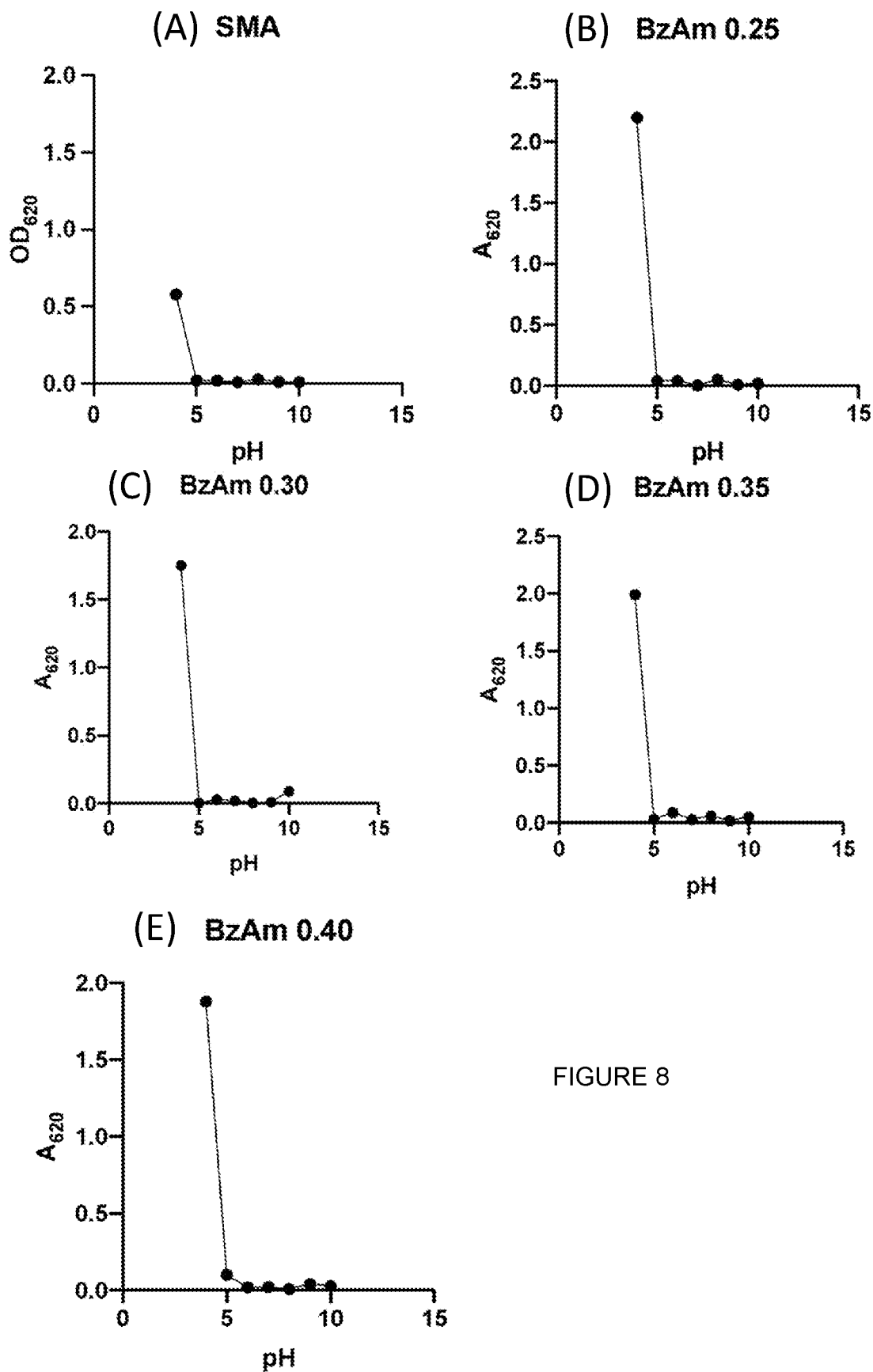
FIG. 8 are plots of the solution turbidity as a function of the pH for (A) SMA 2:1 (control and (B-E) the BzAM-SMA series.

FIG. 8 shows the turbidity results of nanodisc solutions of SMA 2:1 (control) and the BzAm-SMA series as a function of pH. All terpolymers show comparable results to commercial SMA 2:1 being soluble from pH 5 to 10.

Figure 9:
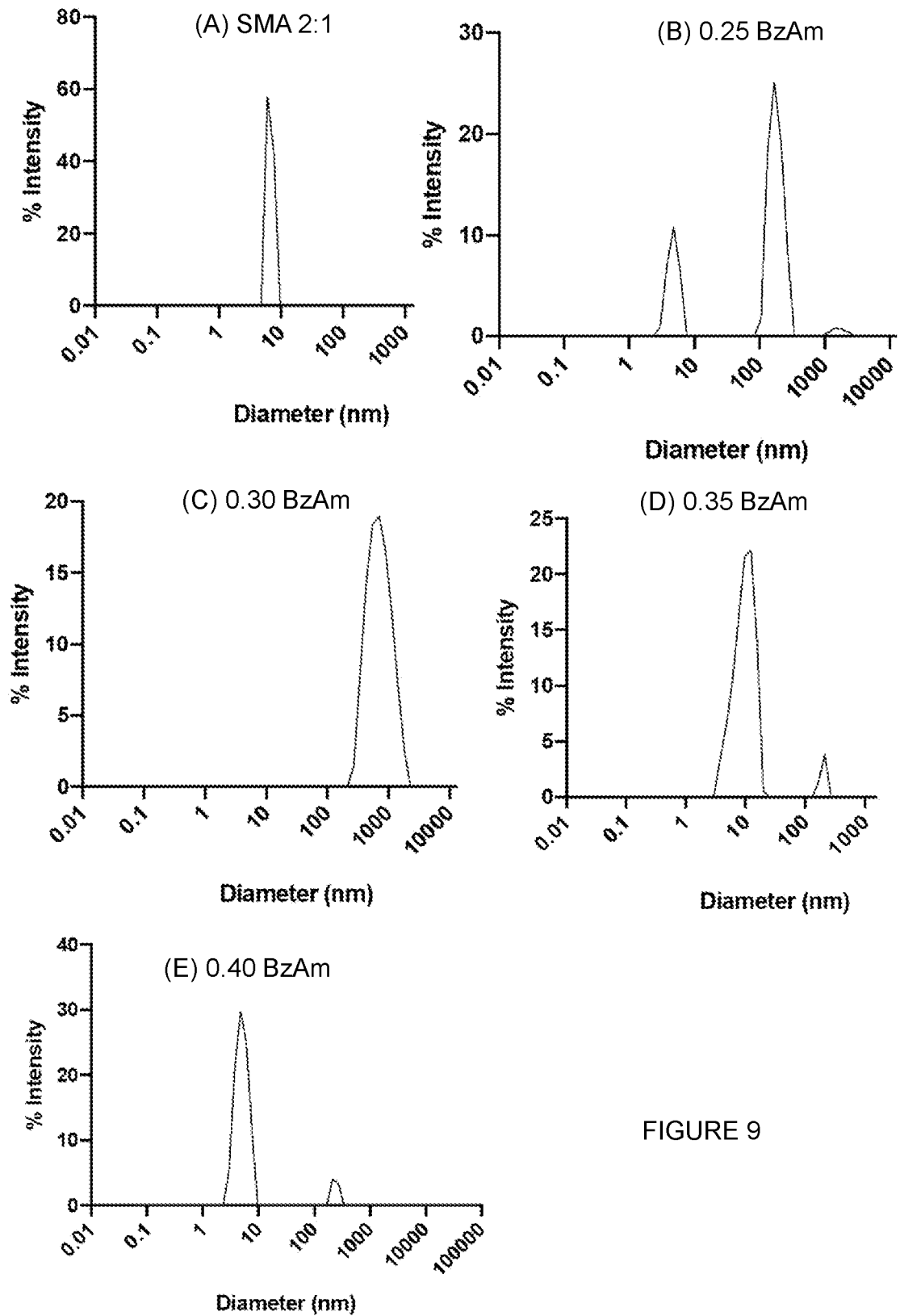
FIG. 9 are plots of the DLS structural analysis of the DMPC nanodiscs formed with (A) SMA 2:1 (control) and (B-E) the BzAm-SMA series at a pH of 5.
Figure 10:
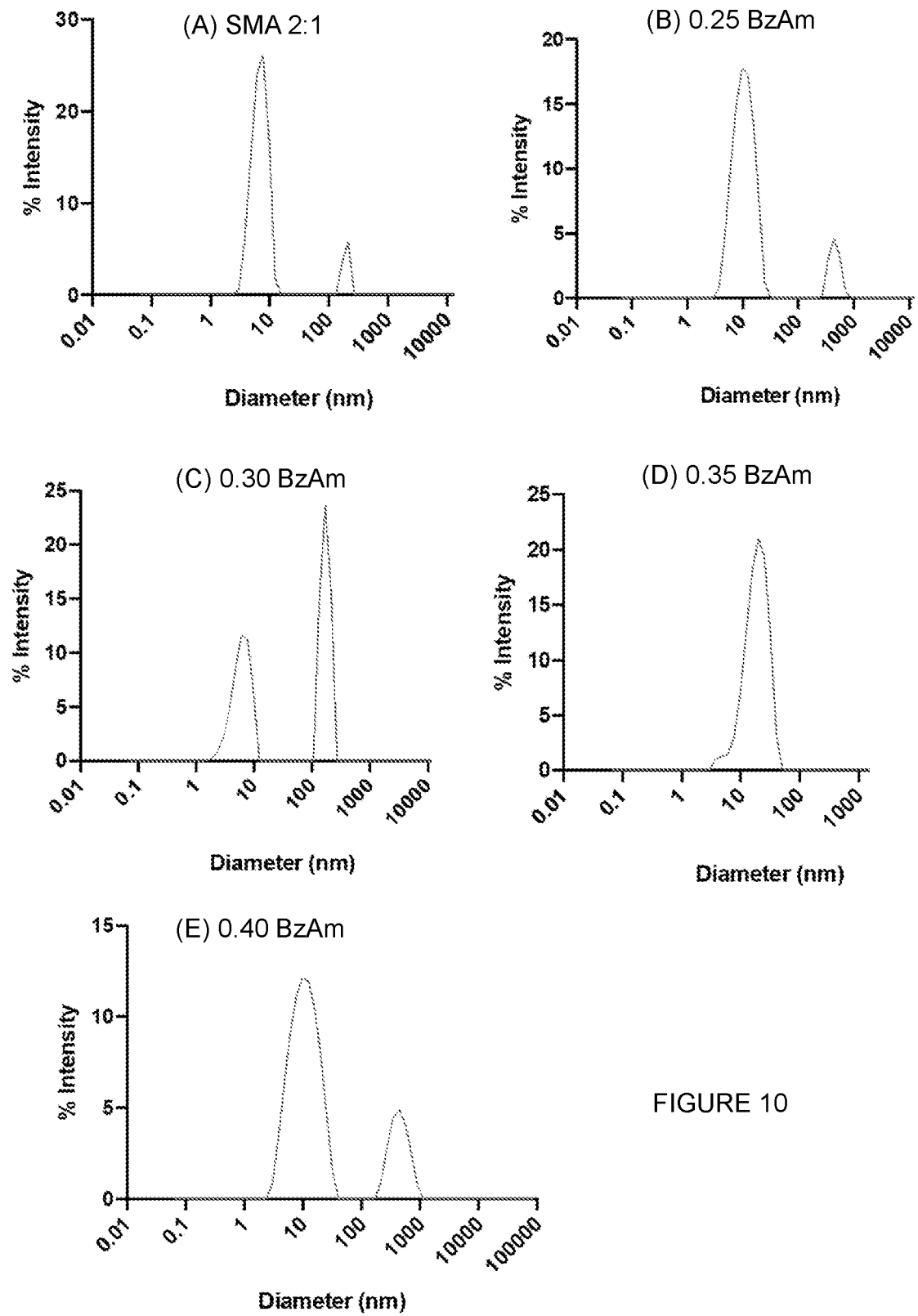
FIG. 10 are plots of the DLS structural analysis of the DMPC nanodiscs formed with (A) SMA 2:1 (control) and (B-E) the BzAm-SMA series at a pH of 6.
Figure 11:
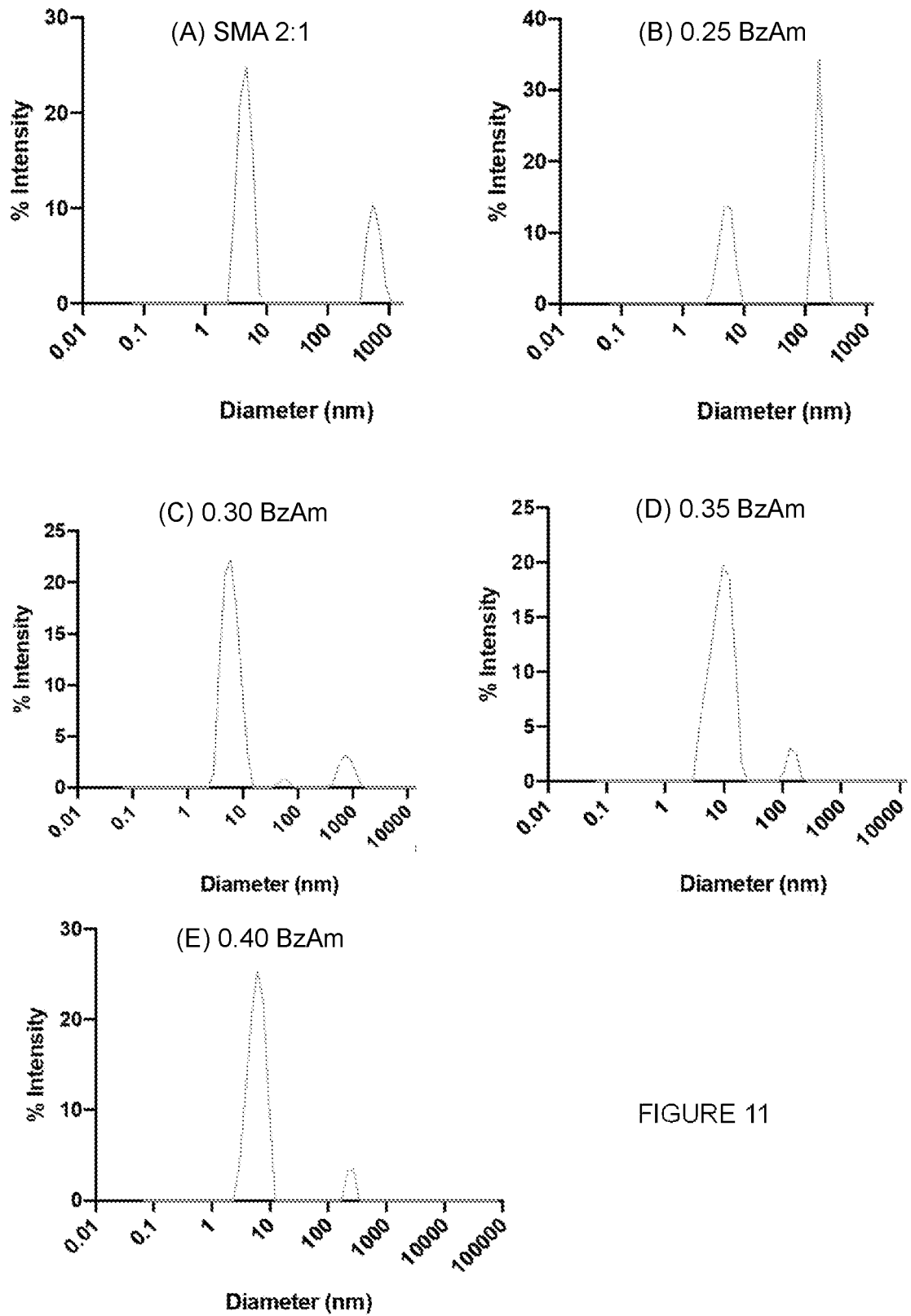
FIG. 11 are plots of the DLS structural analysis of the DMPC nanodiscs formed with (A) SMA 2:1 (control) and (B-E) the BzAm-SMA series at a pH of 7.
Figure 12:
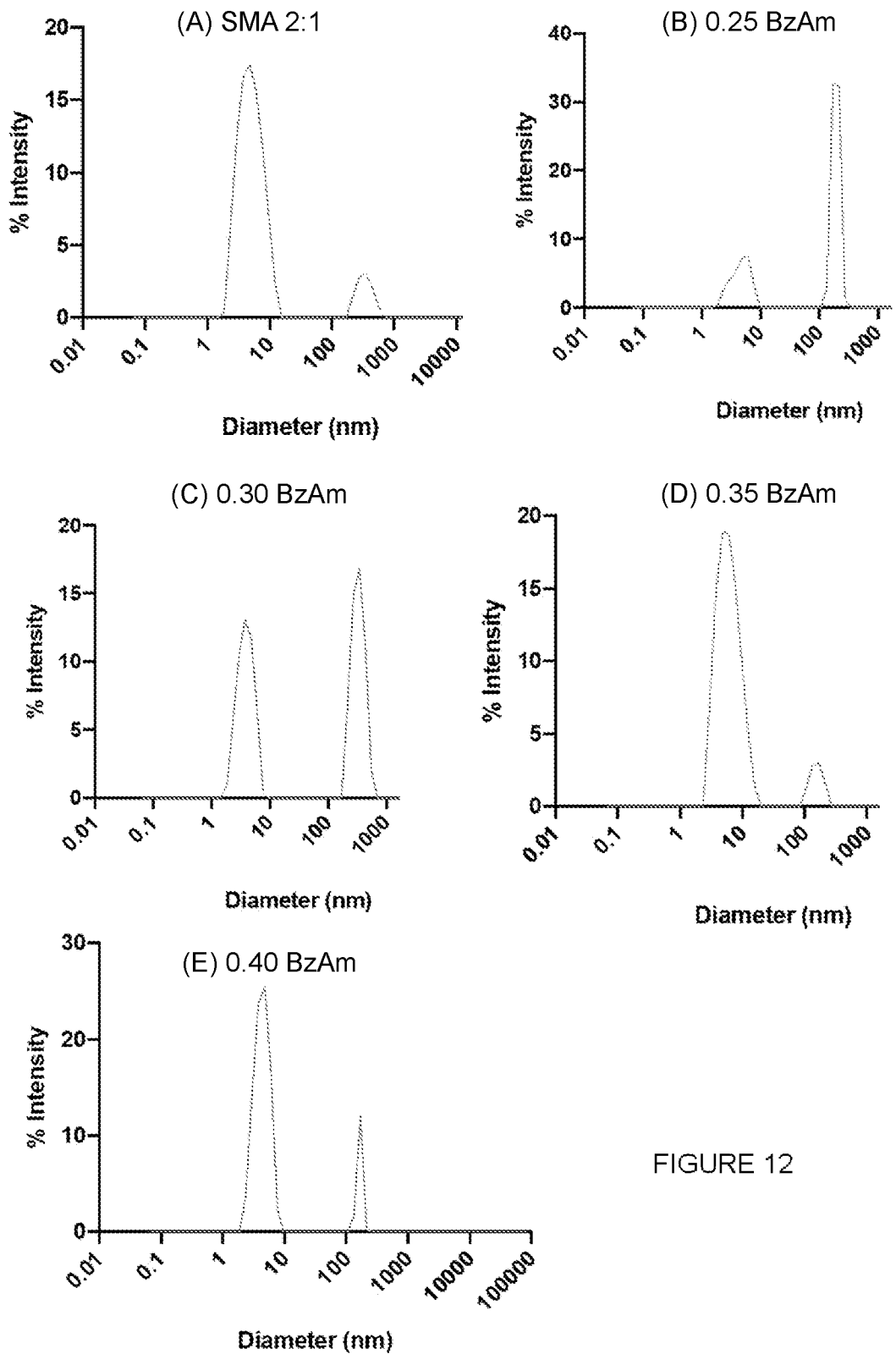
FIG. 12 are plots of the DLS structural analysis of the DMPC nanodiscs formed with (A) SMA 2:1 (control) and (B-E) the BzAm-SMA series at a pH of 8.
Figure 13:
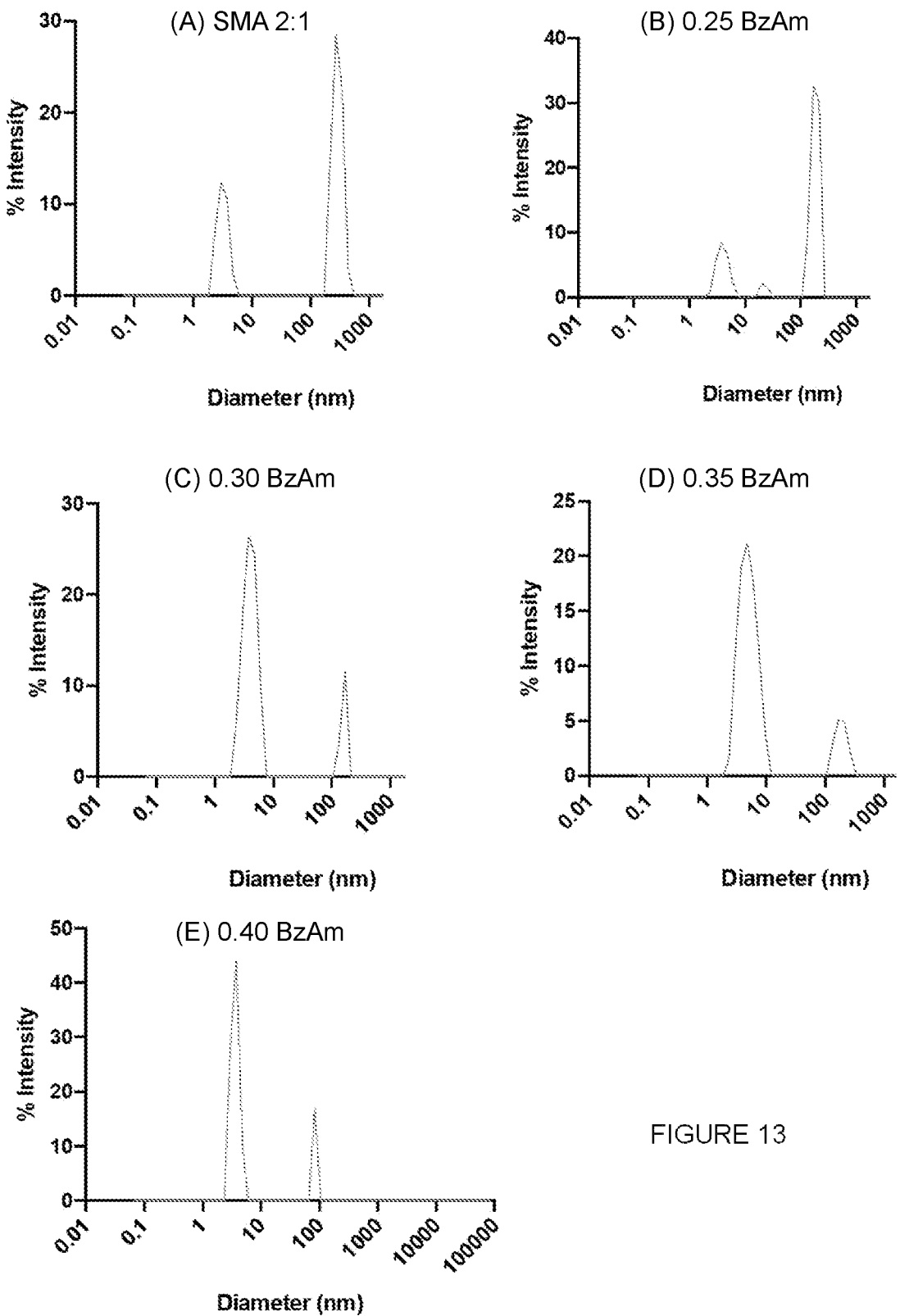
FIG. 13 are plots of the DLS structural analysis of the DMPC nanodiscs formed with (A) SMA 2:1 (control) and (B-E) the BzAm-SMA series at a pH of 9.

FIGS. 9 to 13 illustrate the DLS structural analysis of the DMPC nanodiscs under different pH conditions, showing the intensity-based distributions of DMPC liposome solubilization using SMA 2:1 (control) and the BzAm-SMA series. FIG. 9 shows the DLS structural analysis of the DMPC nanodiscs formed with SMA 2:1 (control) and the BzAm-SMA series at pH 5, FIG. 10 at pH 6, FIG. 11 at pH 7, FIG. 12 at pH 8 and FIG. 13 at pH 9. The first peak at ~10 nm corresponds to the nanodiscs, whereas the second peak at >100 nm corresponds to insolubilized DMPC vesicles. The greater the intensity of the nanodisc peak, the greater the solubilization efficiency of the specific polymer under the specific pH conditions.

Turbidimetric analysis was used to assess the ionic stability of the nanodiscs in the presence of $MgCl_2$ at varying concentrations (0 to 50 mM).

Figure 14:
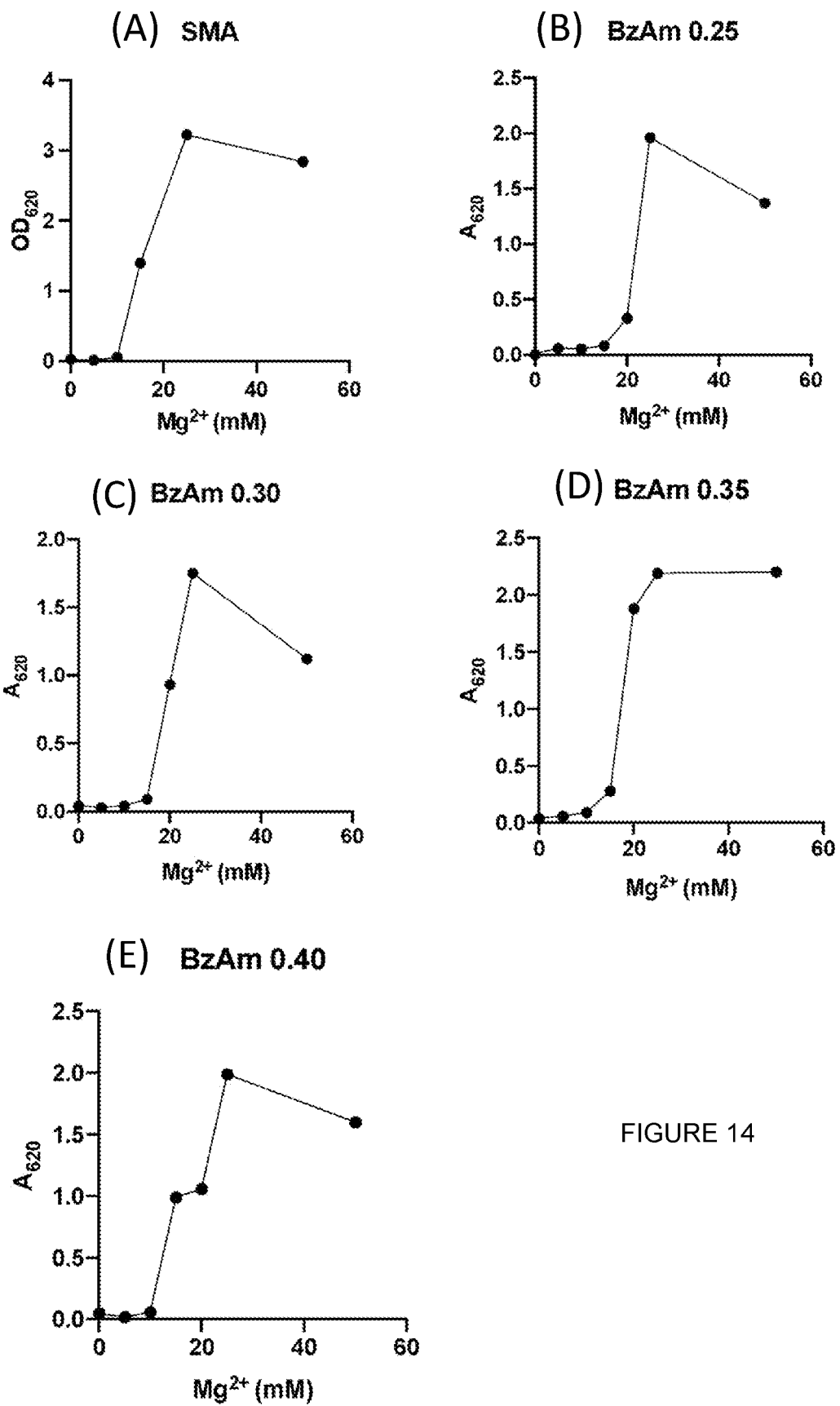
FIG. 14 are plots of the solution turbidity as a function of divalent cation ($Mg^{2+}$) concentration for (A) SMA 2:1 (control) and (B-E) the BzAm-SMA series.

As can be seen in FIG. 14, the 0.25 BzAm-SMA and 0.30 BzAm-SMA samples have the highest $Mg^{2+}$ tolerance. There is a systematic decrease in $Mg^{2+}$ tolerance with increasing percentage (%) modification. This is to be expected as the terpolymer series increases in hydrophobicity. The SMA 2:1 control and the 0.35 and 0.40 BzAm-SMA samples exhibit similar divalent cation ($Mg^{2+}$) tolerance.

Figure 15:
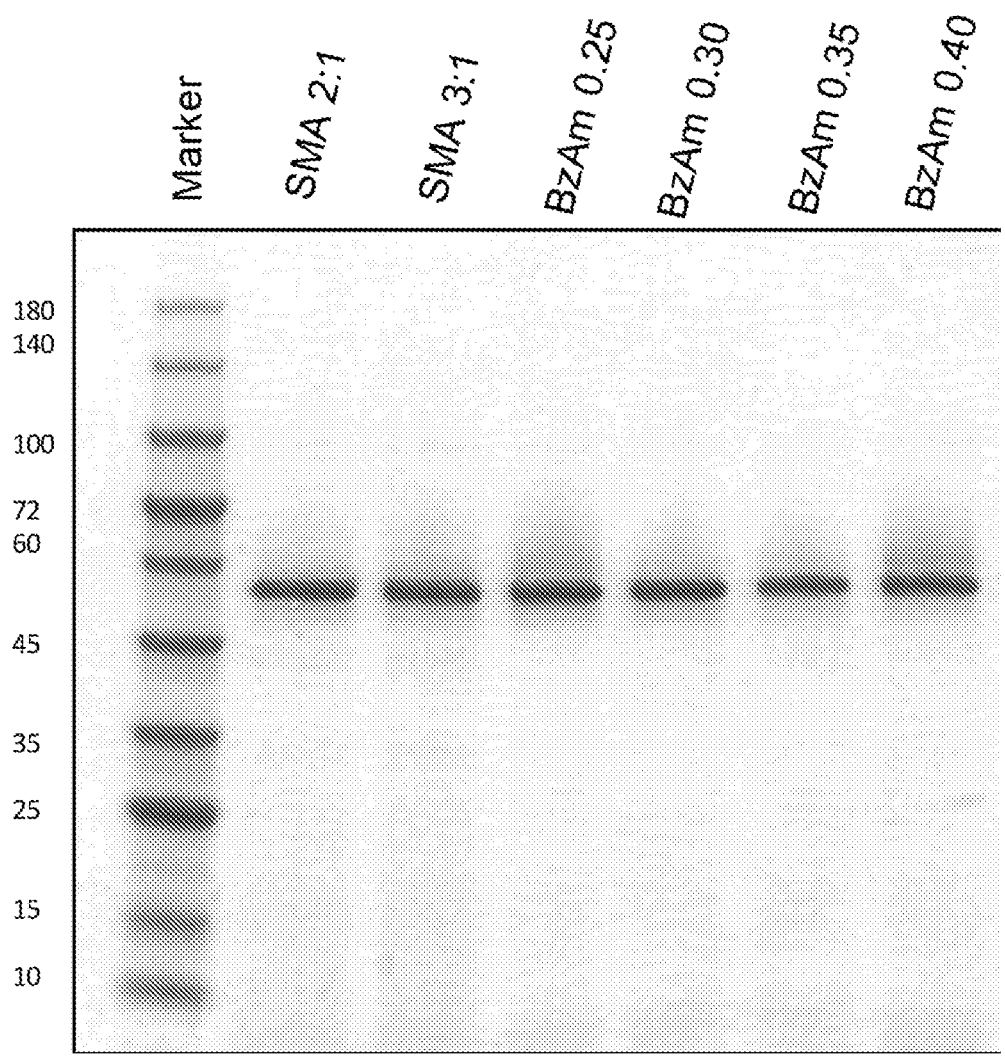
FIG. 15 is a photograph of the gel showing membrane protein (ZipA) solubilisation on SDS-PAGE.

The membrane solubilization efficiency of the BzAm-SMA terpolymer series was assessed through the solubilization of *Escherichia coli* (*E. coli*.) membranes that have been transformed for the overexpression of the transmembrane protein, ZipA. Sodium dodecylsulphate (SDS)-polyacrylamide gel electrophoresis (PAGE) allows for the analysis and separation of proteins according to their respective molecular weights. FIG. 15 shows the solubilization of the ZipA membrane protein on SDS-page. Successful solubilization of ZipA produced a band that migrated with an apparent molecular weight of ~50 KDa. Although ZipA is a 36 kDa single α-helix transmembrane protein, it is known to run aberrantly on SDS-PAGE, thus producing a band at higher molecular weight (Hale, C. A., Rhee, A. C. & de Boer, P. A. J. ZipA-induced bundling of FtsZ polymers mediated by an interaction between C-terminal domains. *Journal of Bacteriology* 182, 5153-5166 (2000)). The performance of commercial SMA 2:1 and SMA 3:1, can be compared to the BzAm-SMA series, where dark, distinct bands are indicative of high purity and high yield solubilization. From these qualitative results, all polymers of the BzAm-SMA series perform as well, if not better, as the commercial variants.

The terpolymers described herein were able to successfully isolate a model membrane protein (ZipA) with high purity, clean bands and in high concentration. The performance of these polymers is comparable to the industry gold standard, SMA2000, indicating successful mimicry with added benefits of a more defined polymeric material.

Advantageously, the amphiphilicity of the terpolymers described herein may be varied by varying the extent and type of derivatization of the maleic anhydride repeat units in the parent polymer backbone, making the terpolymer series produced suitable for a variety of different SMALP applications. The terpolymer series is easy to make using RAFT polymerisation and easy to tune in terms of amphiphilicity. The degree of modification of the polymers may also affect nanodisc size. Accordingly, the terpolymer series also provides a way of tuning nanodisc size as may be required for a specific application.

The use of a narrow molecular weight distribution terpolymers to isolate membrane proteins from membranes or other lipid structures means that no additional purification or extraction steps are required to produce clean or distinct bands on the electrophoresis gel.

Furthermore, the use of controlled polymerization techniques such as RAFT not only allows for the production of narrow MMD polymers with predefined properties, but also allows for the facile introduction of chain-end functionalities in the polymer. This proved to be very beneficial for added functionality of the nanodiscs (fluorescent labelling, surface immobilization, etc), which is not an option for conventionally produced polymers such as the commercial variants. Commercial SMA cannot be easily functionalised at its chain end, which means that the introduction of a single functionality per polymer chain is cumbersome. This leads to limitations when it comes to immobilization on a surface, attachment of a biotin for biotin-streptavidin conjugation and the like.

The foregoing description has been presented for the purpose of illustration; it is not intended to be exhaustive or to limit the invention to the precise forms disclosed. Persons skilled in the relevant art can appreciate that many modifications and variations are possible in light of the above disclosure.

The language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

Finally, throughout the specification and accompanying claims, unless the context requires otherwise, the word 'comprise' or variations such as 'comprises' or 'comprising' will be understood to imply the inclusion of a stated integer or group of integers but not the exclusion of any other integer or group of integers.

The invention claimed is:

1. A terpolymer comprising styrene repeat units, which are optionally partially substituted, N-alkylmaleimide repeat units and repeat units selected from the group consisting of maleic anhydride repeat units, maleic acid repeat units or maleic anhydride derivative repeat units, wherein the styrene repeat units which are optionally partially substituted are present in a mol fraction between and including 0.50 and 0.55, and wherein the terpolymer has a narrow molecular weight distribution characterised by a dispersity (Đ) of less than or equal to 1.4 as determined by size exclusion chromatography using N,N-dimethylformamide as mobile phase.

2. The terpolymer as claimed in claim 1, wherein the N-alkylmaleimide repeat units are N-benzylmaleimide repeat units.

3. The terpolymer as claimed in claim 1, wherein the maleic anhydride derivative repeat units are alkyl maleates, N-alkyl maleimide derivatives with a different alkyl group to that of the N-alkylmaleimide repeat units, N—(N',N'-disubstituted amino-alkyl)-maleimide) derivatives or maleic anhydride derivatives including a zwitterionic moiety.

4. The terpolymer as claimed in claim 3, wherein the zwitterionic moiety is selected from the group consisting of carboxybetaines, sulfobetaines or phosphobetaines.

5. The terpolymer as claimed in claim 1, wherein the mole fraction of N-alkylmaleimide repeat units in the terpolymer is between and including 0.05 and 0.40.

6. The terpolymer as claimed in claim 1, having the general structure of formula (I):

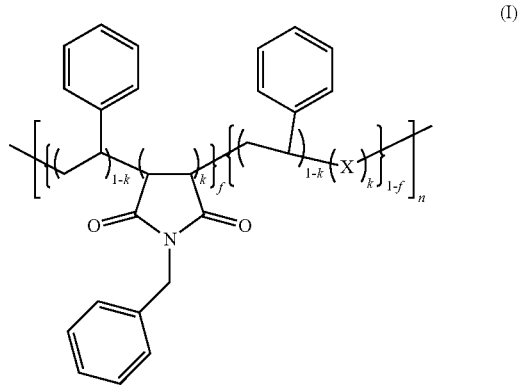

in which f is between and including 0.05 and 0.40, k is between and including 0.45 and 0.50, n is between and including 5 and 45, and X is selected from the group consisting of

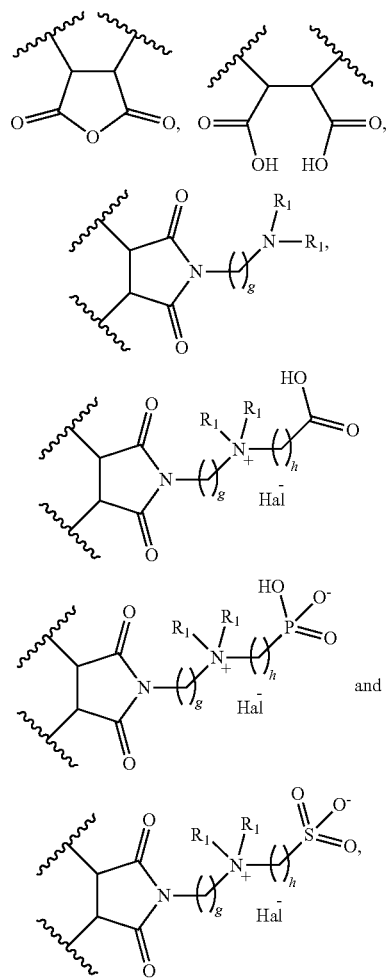

in which g is an integer between and including 2 and 7;
h is an integer between and including 1 and 6;
$R_1$ is a branched or linear $C_1$-$C_4$ alkyl; and
Hal⁻ is a halide anion selected from the group consisting of bromide (Br⁻), chloride (Cl⁻) and iodide (I⁻).

7. The terpolymer as claimed in claim 6, wherein g is 2 or 3 and h is 2 or 3.

8. The terpolymer as claimed in claim 6, wherein $R_1$ is a methyl or ethyl group.

9. The terpolymer as claimed in claim 6, wherein X is

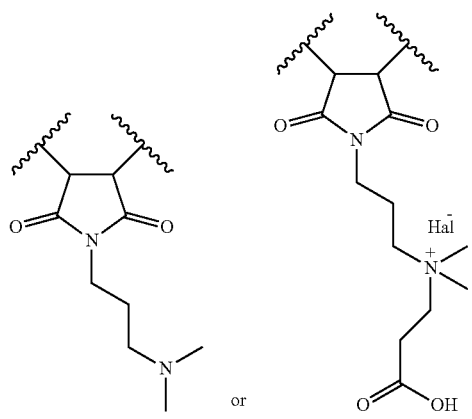

in which Hal⁻ is a halide anion selected from (Br⁻), chloride (Cl⁻) and iodide (I⁻).

10. A method of synthesizing a terpolymer comprising styrene repeat units which are optionally partially substituted, N-alkylmaleimide repeat units and repeat units selected from the group consisting of maleic anhydride repeat units, maleic acid repeat units or maleic anhydride derivative repeat units, wherein the styrene repeat units which are optionally partially substituted are present in a mol fraction between and including 0.50 and 0.55, and wherein the terpolymer has a narrow molecular weight distribution characterised by a dispersity (Đ) of less than or equal to 1.4 as determined by size exclusion chromatography using N,N-dimethylformamide as mobile phase, the method comprising the steps of:
reacting a precursor copolymer of styrene repeat units which are optionally partially substituted and present in a mol fraction between and including 0.50 and 0.55, and maleic anhydride repeat units, and having a narrow molecular weight distribution characterized by a dispersity (Đ) of less than or equal to 1.4 with a selected molar amount of alkyl amine to form a terpolymer which includes a selected mole fraction of N-alkylmaleimide repeat units; and
optionally hydrolysing or further modifying remaining maleic anhydride repeat units in the terpolymer.

11. The method as claimed in claim 10, wherein the molar amount of alkyl amine added is selected to produce a partially derivatized terpolymer in which the mole fraction (f) of N-alkylmaleimide repeat units ranges between and including 0.05 and 0.40.

12. The method as claimed in claim 10, wherein the precursor copolymer is a RAFT-polymerized substantially alternating styrene maleic anhydride (SMAnh) copolymer.

13. The method as claimed in claim 12, wherein the RAFT moiety end group of the RAFT-polymerized styrene maleic anhydride (SMAnh) polymer is removed prior to the reaction with alkyl amine to form the terpolymer.

14. The method as claimed in claim 10, wherein the remaining maleic anhydride repeat units are modified to N-alkyl maleimide derivative repeat units with a different alkyl group to that of the N-alkylmaleimide repeat units.

15. The method as claimed in claim 10, wherein the remaining maleic anhydride repeat units are modified to N—(N',N'-disubstituted amino-alkyl)-maleimide) derivative repeat units.

16. The method as claimed in claim 15, wherein the remaining maleic anhydride repeat units are imidized to N—(N',N'-dimethyl-3-aminopropyl)-maleimide repeat units by reacting the terpolymer with 3-(N,—N-dimethylamino) propyl-1-amine (DMAPA).

17. The method as claimed in claim 10, wherein the remaining maleic anhydride repeat units are modified to include a zwitterionic moiety selected from the group consisting of a carboxybetaine, sulfobetaine or phosphobetaine.

18. The method as claimed in claim 17, wherein the carboxybetaine moiety is an ammoniocarboxylate formed by reacting the terpolymer with N,N-disubstituted aminoalkyl-1-amine to obtain a modified terpolymer in which the maleic anhydride repeat units have been imidized to N—(N', N'-disubstituted amino-alkyl)-maleimide) repeat units and reacting the modified terpolymer with a ω-halo-alkanoic acid to produce a terpolymer including zwitterionic ammoniocarboxylate moieties.

19. A method of isolating a membrane protein from a lipid bilayer, the method comprising mixing the lipid membrane including a membrane protein with an aqueous solution of a terpolymer as claimed in claim 1 to produce nanodiscs.

20. A method of solubilising a lipid bilayer optionally including one or more membrane proteins, the method comprising mixing the lipid bilayer with an aqueous solution of a terpolymer as claimed in claim 1 to produce nanodiscs.

* * * * *